United States Patent
Davis et al.

(10) Patent No.: US 10,866,236 B2
(45) Date of Patent: Dec. 15, 2020

(54) DETECTION OF CLEAVAGE ACTIVITY OF AN ENZYME

(71) Applicant: Mologic Limited, Thurleigh (GB)

(72) Inventors: Paul Davis, Sharnbrook (GB); Gita Parekh, Milton Keynes (GB); James Schouten, Thurleigh (GB)

(73) Assignee: Mologic Limited, Bedfordshire (GB)

(*) Notice: Subject to any disclaimer, the term of this patent is extended or adjusted under 35 U.S.C. 154(b) by 572 days.

(21) Appl. No.: 15/031,600

(22) PCT Filed: Oct. 23, 2014

(86) PCT No.: PCT/GB2014/053171
§ 371 (c)(1),
(2) Date: Apr. 22, 2016

(87) PCT Pub. No.: WO2015/059487
PCT Pub. Date: Apr. 30, 2015

(65) Prior Publication Data
US 2016/0238596 A1    Aug. 18, 2016

(30) Foreign Application Priority Data
Oct. 23, 2013 (GB) .................................. 1318728.1

(51) Int. Cl.
| G01N 33/573 | (2006.01) |
| G01N 33/543 | (2006.01) |
| G01N 33/558 | (2006.01) |
| C12Q 1/37 | (2006.01) |

(52) U.S. Cl.
CPC ......... *G01N 33/54386* (2013.01); *C12Q 1/37* (2013.01); *G01N 33/558* (2013.01); *G01N 33/573* (2013.01); *G01N 2333/96486* (2013.01); *G01N 2800/12* (2013.01); *G01N 2800/382* (2013.01)

(58) Field of Classification Search
USPC .......................................................... 435/7.4
See application file for complete search history.

(56) References Cited

U.S. PATENT DOCUMENTS

| 4,795,702 A | 1/1989 | Blake | |
| 2009/0053738 A1* | 2/2009 | Davis ................... | G01N 33/573 435/7.4 |

FOREIGN PATENT DOCUMENTS

| EP | 1889919 A1 | 2/2008 |
| GB | 2435511 A | 8/2007 |
| GB | 2437311 A | 10/2007 |

(Continued)

OTHER PUBLICATIONS

Examination Report for GB1318728.1 dated Jul. 22, 2014.
(Continued)

*Primary Examiner* — Christopher L Chin
(74) *Attorney, Agent, or Firm* — Quarles & Brady LLP

(57) ABSTRACT

The present invention relates to detecting cleavage activity of an enzyme. The various aspects of the invention include an enzyme detection device, kit, method and use for detecting or measuring the presence in a test sample of the activity of an enzyme capable of cleaving a substrate. The invention also relates to indicator and binding molecules useful for carrying out the invention. The enzyme substrate contains a hidden binding site which is only revealed upon cleavage by the enzyme.

1 Claim, 28 Drawing Sheets
Specification includes a Sequence Listing.

(56) References Cited

FOREIGN PATENT DOCUMENTS

| | | | |
|---|---|---|---|
| WO | 03102544 A2 | 12/2003 | |
| WO | 2004077062 A2 | 9/2004 | |
| WO | 2004099784 A2 | 11/2004 | |
| WO | 2004104219 A1 | 12/2004 | |
| WO | 2005024050 A1 | 3/2005 | |
| WO | WO 2005024050 A1 * | 3/2005 | ............... C12Q 1/37 |
| WO | 2007128980 A1 | 11/2007 | |
| WO | 2008075214 A1 | 6/2008 | |
| WO | 2012154272 A1 | 11/2012 | |
| WO | WO-2012154272 A1 * | 11/2012 | ........... G01N 33/573 |
| WO | 2013116791 A1 | 8/2013 | |
| WO | 2013156795 A1 | 10/2013 | |

OTHER PUBLICATIONS

International Search Report and Written Opinion for PCT/GB2014/053171 dated Apr. 30, 2015.
International Preliminary Report on Patentability for PCT/GB2014/053171 dated Jan. 2, 2016.
European Office Action for EP14790689.5 dated Nov. 2, 2017.
First Chinese Office Action for CH201480067890.6 dated Aug. 4, 2017.
Japanese Office Action dated Sep. 12, 2018.
Chinese Office Action dated Jun. 19, 2018.

* cited by examiner

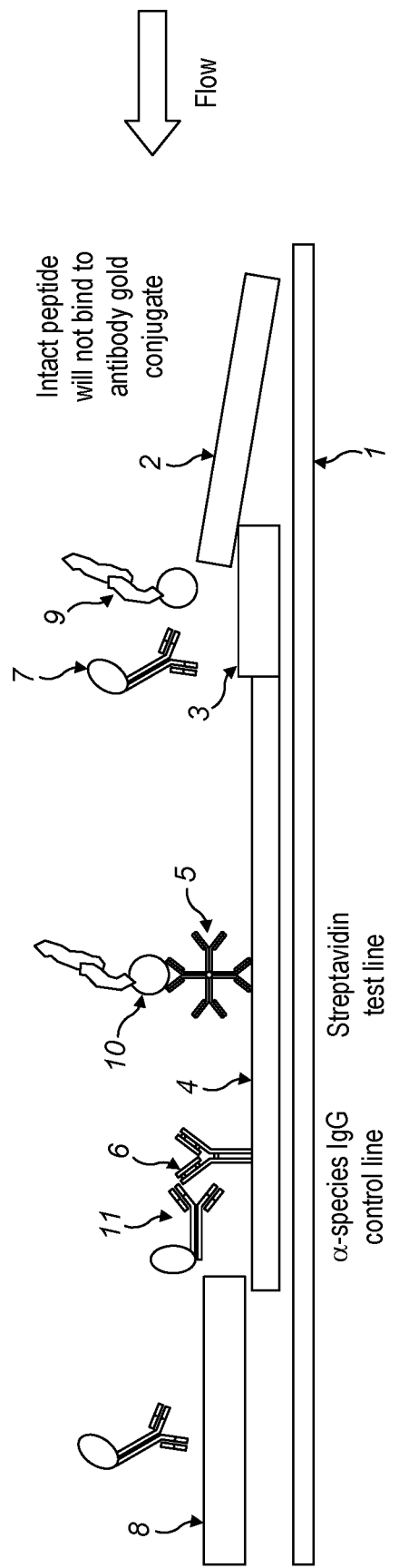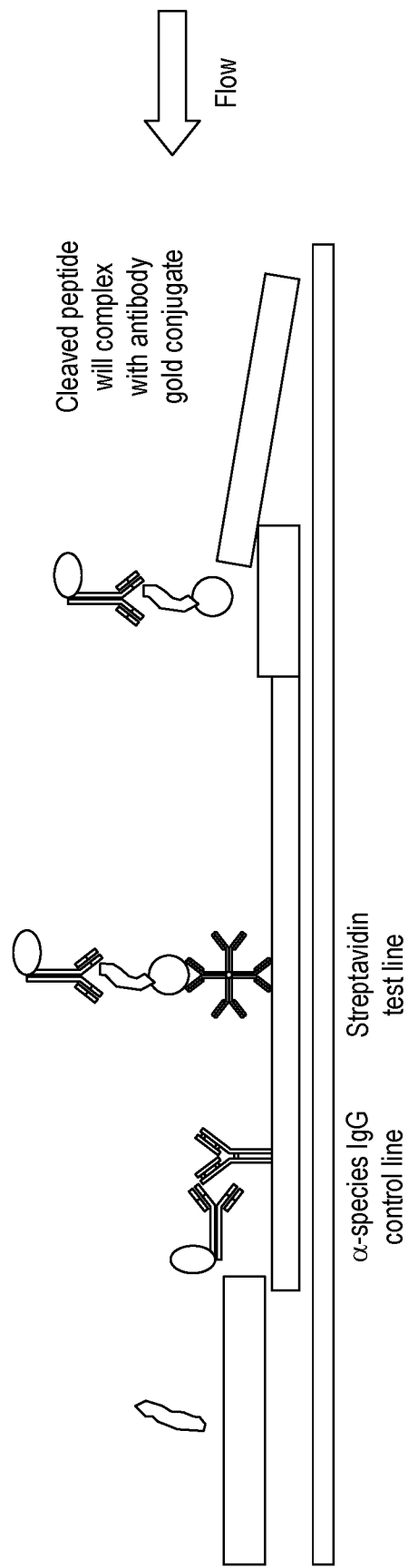

1,2-bis(Bromomethyl) benzene
1,3-bis(Bromomethyl) benzene
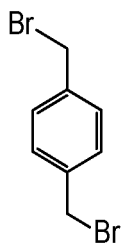
1,4-bis(Bromomethyl) benzene
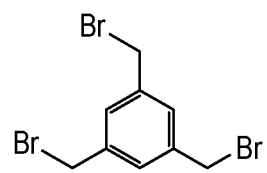
1,3,5-tris(Bromomethyl) benzene
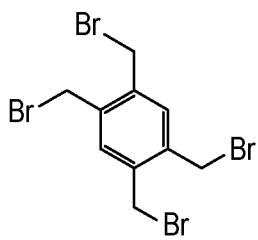
1,2,4,5-tetrakis(Bromomethyl) benzene
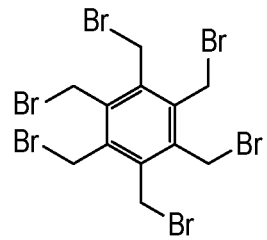
1,2,3,4,5,6-hexakis(Bromomethyl) benzene
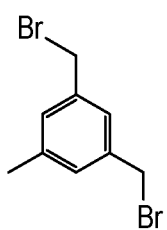
1,3-bis(bromomethyl)-5-methylbenzene
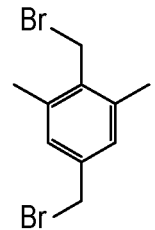
2,5-bis(bromomethyl)-1,3-dimethylbenzene
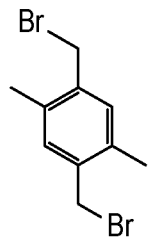
2,5-bis(bromomethyl)-1,4-dimethylbenzene
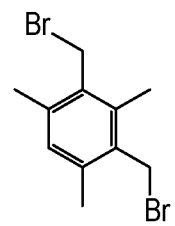
2,5-bis(bromomethyl)-1,4-dimethylbenzene
FIG. 14

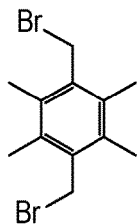
3,6-bis(bromomethyl)durene
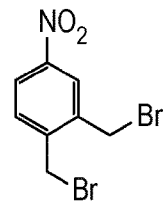
3,4-bis(bromomethyl)-nitrobenzene
2,3-bis(bromomethyl)-nitrobenzene
2,6-bis(bromomethyl)-benzonitrile
1,3-bis(bromomethyl)-5-methoxybenzene
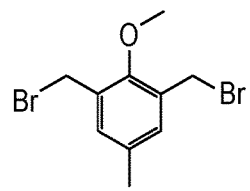
1,3-bis(bromomethyl)-2-methoxy-5-methylbenzene
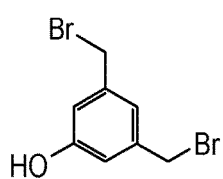
1,3-bis(bromomethyl)-5-hydroxybenzene
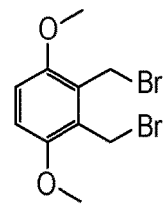
2,3-bis(bromomethyl)-1,4-dimethoxybenzene
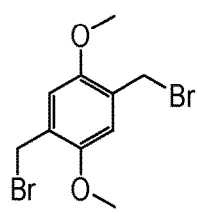
2,5-bis(bromomethyl)-1,4-dimethoxybenzene
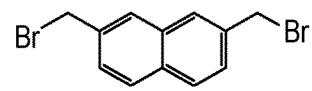
2,7-bis(bromomethyl)-naphthalene
FIG. 14 Cont'd

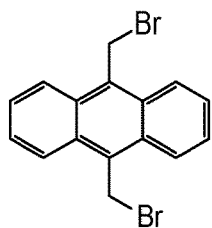
1,4-bis(bromomethyl)-anthracene
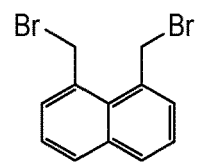
1,8-bis(bromomethyl)-naphthalene
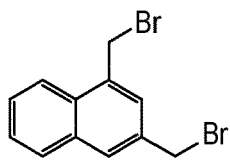
1,3-bis(bromomethyl)-naphthalene
1,2-bis(bromomethyl)-naphthalene
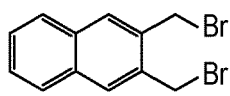
2,3-bis(bromomethyl)-naphthalene
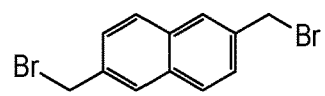
2,6-bis(bromomethyl)-naphthalene
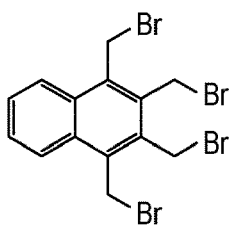
1,2,3,4-tetrakis(bromomethyl)-naphthalene
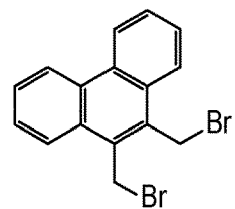
9,10-bis(bromomethyl)-phenanthrene
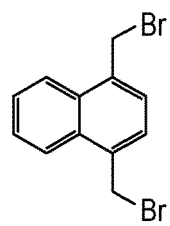
1,4-bis(bromomethyl)-naphthalene
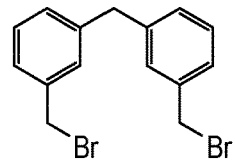
1-(bromomethyl)-3-[3(bromoethyl)benzyl]benzene
*FIG. 14 Cont'd*

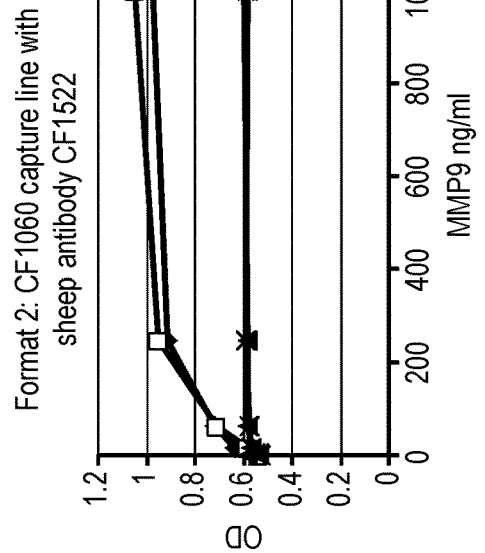
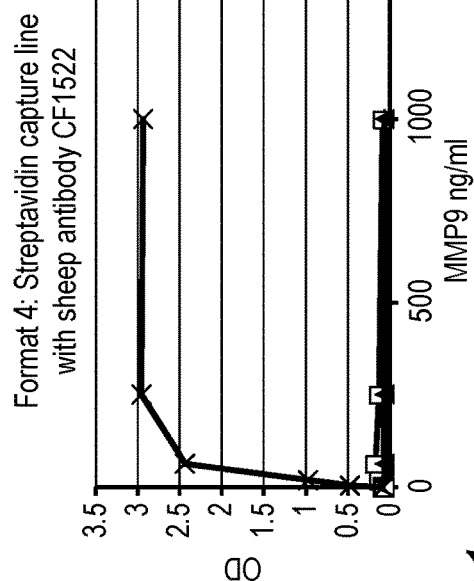
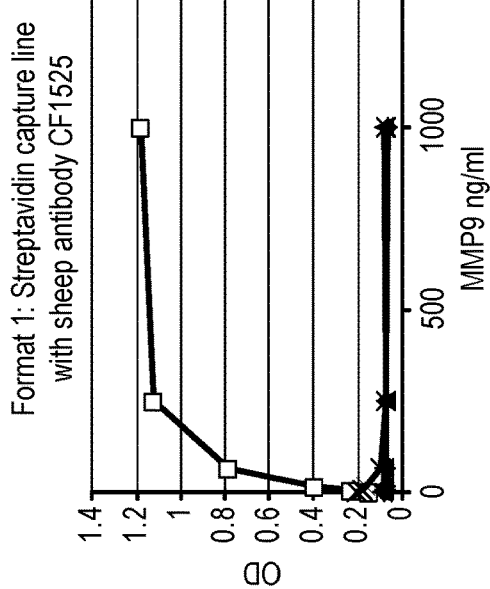
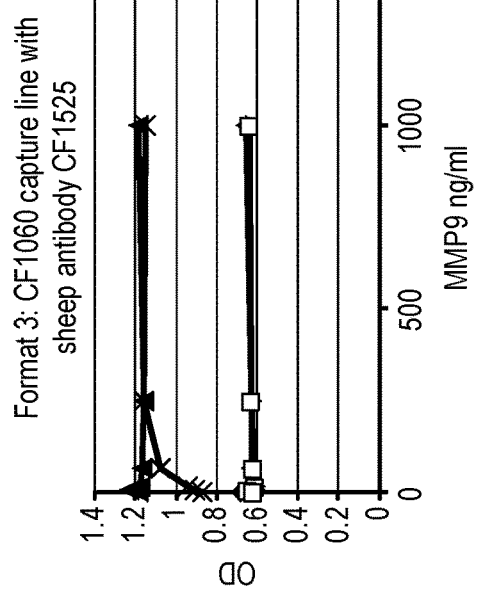
FIG. 21

SEQUENCE LISTING

<160> NUMBER OF SEQ ID NOS: 4

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Gly Pro Gln Gly Ile Phe Gly Gln
1               5

<210> SEQ ID NO 2
<211> LENGTH: 10
<212> TYPE: PRT
<213> ORGANISM: Artificial sequence
<220> FEATURE:
<223> OTHER INFORMATION: Synthetic peptide

<400> SEQUENCE: 2

Cys Gly Pro Gln Gly Ile Phe Gly Gln Cys
1               5                   10

<210> SEQ ID NO 3
<211> LENGTH: 10
<212> TYPE: PRT
<213> ORGANISM: Artificial sequence
<220> FEATURE:
<223> OTHER INFORMATION: Synthetic peptide

<400> SEQUENCE: 3

Cys Gln Glu Ser Ile Arg Leu Pro Gly Cys
1               5                   10

<210> SEQ ID NO 4
<211> LENGTH: 11
<212> TYPE: PRT
<213> ORGANISM: Artificial sequence
<220> FEATURE:
<223> OTHER INFORMATION: Synthetic peptide

<400> SEQUENCE: 4

Tyr Cys Gln Glu Ser Ile Arg Leu Pro Gly Cys
1               5                   10

DETECTION OF CLEAVAGE ACTIVITY OF AN ENZYME

CROSS REFERENCE TO RELATED APPLICATION

The present application is the U.S. national stage of International Application PCT/GB2014/053171, filed Oct. 23, 2014, which international application was published on Apr. 30, 2015 as International Publication No. WO 2015/059487. The International Application claims priority to British Patent Application No. 1318728.1, filed Oct. 23, 2013, the contents of which are incorporated herein by reference in their entireties.

FIELD OF THE INVENTION

The present invention relates to detecting cleavage activity of an enzyme. The various aspects of the invention include an enzyme detection device, kit, method and use for detecting or measuring the presence in a test sample of the activity of an enzyme capable of cleaving a substrate. The invention also relates to indicator and binding molecules useful for carrying out the invention.

BACKGROUND TO THE INVENTION

Enzymes constitute a family of proteins involved in catalysing chemical reactions within living organisms. As a result of their importance, there are numerous situations in which it is necessary and/or beneficial to measure enzyme levels, and importantly, enzyme activity.

In particular, increases in enzyme activity have been found to correlate with specific conditions and/or diseases. For example up-regulated protease activity has been associated with many aspects of cancer progression. The measurement of enzyme activity in samples taken from individuals with a particular condition or suspected of having a specific condition or disease may therefore be useful for prognostic or diagnostic purposes.

Within the enzyme family, there are many classes of enzyme that act by facilitating substrate cleavage. For example, peptidases and proteases catalyse the hydrolysis of peptide bonds within their respective substrates. In the past, researchers have, in some cases, sought to measure this type of activity using kits or devices that measure release of a fragment or 'leaving group' from the initial enzyme substrate.

Assays based on this fundamental principle have been refined such that in some cases, inventors have described engineered substrate molecules linked to reporter moieties. Cleavage of the substrate by the enzyme to be detected, if present, leads to release of said reporter, which can be detected by a range of techniques available to those skilled in the art. An assay of this type is described for example in US2006/0003394.

Others have sought to develop assays for the measurement of enzyme activity based around the principle of discriminating between modified and unmodified forms of an enzyme substrate. In this regard, WO2009/024805 describes an enzyme detection device utilising a "substrate recognition molecule" (SRM) carrying a detectable label, wherein the SRM specifically binds to the enzyme substrate in the unmodified state and in doing so presents binding of the enzyme to the substrate.

U.S. Pat. No. 5,171,662 describes methods for identifying compounds that inhibit HIV protease. The methods are based on a competitive binding radioimmunoassay. US 2005/0164311 describes methods for detecting reaction products to indicate the presence of a reaction product inducer such as an enzyme.

DESCRIPTION OF THE INVENTION

The present invention results from attempts to improve sensitivity and/or specificity of protease activity detection. In particular, in certain test samples such as urine and environmental samples, proteases may be present in extremely low concentrations. The devices and methods described herein aim to permit detection of protease activity at low levels or concentrations. It has been found that use of binding molecules, such as antibodies, that bind only to specific products of cleavage but not to the uncleaved indicator molecule, enable detection of protease activity at low concentrations in test samples (in particular urine samples). In the context of the claimed flow devices, specific assays can be performed where the reagents can be employed in excess without impacting on specificity of detection. It is also shown herein that the claimed flow devices provide diagnostically useful results, where comparable enzyme immunocapture and activity assays do not. Without being bound by theory this may be due to differing binding efficiencies throughout the different processes.

Accordingly, in one aspect, the invention provides an enzyme detection device for detecting the presence in a test sample of cleavage activity of an enzyme capable of cleaving a substrate, the device comprising:
(i) an indicator molecule for adding to the test sample, said indicator molecule comprising
(a) a cleavage region comprising at least one cleavage site, which can be cleaved by said enzyme if said enzyme cleavage activity is present; and
(b) a capture site;
wherein cleavage of the at least one cleavage site produces a novel binding site;
(ii) a capture zone to receive the test sample, wherein the capture zone comprises capture molecules capable of binding to the capture site of the indicator molecule in order to immobilise the indicator molecule including the novel binding site; and
(iii) binding molecules capable of binding to the novel binding site, wherein the binding molecules are incapable of binding to the indicator molecule unless and until cleavage has occurred.

Similarly, the invention provides an enzyme detection device for detecting the presence in a test sample of cleavage activity of an enzyme capable of cleaving a substrate, the device comprising:
(i) an indicator molecule for adding to the test sample, said indicator molecule comprising
  (a) a cleavage region comprising at least one cleavage site, which can be cleaved by said enzyme if said enzyme cleavage activity is present; and
  (b) a capture site;
wherein cleavage of the at least one cleavage site produces at least two parts of the cleavage region, at least one part of which remains connected to the capture site;
(ii) a capture zone to receive the test sample, wherein the capture zone comprises capture molecules capable of binding to the capture site of the indicator molecule; and
(iii) binding molecules capable of binding to the part of the indicator molecule containing the at least one part of the cleavage region connected to the capture site, wherein the binding molecules are incapable of binding to the indicator molecule unless and until cleavage has occurred.

The two parts of the cleavage region are thus separated from one another at the site of cleavage. The cleavage event at the site of the cleavage produces the novel binding site The invention further provides a method for detecting the presence or absence in a test sample of cleavage activity of an enzyme capable of cleaving a substrate, the method comprising:
(i) bringing an indicator molecule into contact with the test sample, said indicator molecule comprising
(a) a cleavage region comprising at least one cleavage site, which can be cleaved by said enzyme if said enzyme cleavage activity is present; and
(b) a capture site;
wherein cleavage of the at least one cleavage site produces a novel binding site;
(ii) adding to the test sample binding molecules capable of binding to the novel binding site, wherein the binding molecules are incapable of binding to the indicator molecule unless and until cleavage has occurred;
(iii) capturing the part of the indicator molecule containing the novel binding site at a capture zone through binding of capture molecules in the capture zone to the capture site; and
(iv) detecting cleavage of the at least one cleavage site by determining binding of the binding molecules to the novel binding site of the indicator molecule captured in the capture zone.

Similarly, the invention also provides a method for detecting the presence or absence in a test sample of cleavage activity of an enzyme capable of cleaving a substrate, the method comprising:
(i) bringing an indicator molecule into contact with the test sample, said indicator molecule comprising
   (a) a cleavage region comprising at least one cleavage site, which can be cleaved by said enzyme if said enzyme cleavage activity is present; and
   (b) a capture site
wherein cleavage of the at least one cleavage site produces at least two parts of the cleavage region, at least one part of which remains connected to the capture site;
(ii) adding to the test sample binding molecules capable of binding to the part of the indicator molecule containing the at least one part of the cleavage region connected to the capture site, wherein the binding molecules are incapable of binding to the indicator molecule unless and until cleavage has occurred;
(iii) capturing the part of the indicator molecule containing the at least one part of the cleavage region connected to the capture site at a capture zone through binding of capture molecules in the capture zone to the capture site; and
(iv) detecting cleavage of the at least one cleavage site by determining binding of the binding molecules to the part of the indicator molecule captured in the capture zone.

The devices and methods of the invention have been shown by the inventors to have specific application in the field of diagnosis of respiratory conditions. Thus, the invention further provides a method for diagnosing (the presence or absence of) a respiratory condition in a test sample by detecting cleavage activity of an enzyme capable of cleaving a substrate, the method comprising:
(i) bringing an indicator molecule into contact with the test sample, said indicator molecule comprising
(a) a cleavage region comprising at least one cleavage site, which can be cleaved by said enzyme if said enzyme cleavage activity is present; and
(b) a capture site;
wherein cleavage of the at least one cleavage site produces a novel binding site;
(ii) adding to the test sample binding molecules capable of binding to the novel binding site, wherein the binding molecules are incapable of binding to the indicator molecule unless and until cleavage has occurred;
(iii) capturing the part of the indicator molecule containing the novel binding site at a capture zone through binding of capture molecules in the capture zone to the capture site; and
(iv) detecting cleavage of the at least one cleavage site by determining binding of the binding molecules to the novel binding site of the indicator molecule captured in the capture zone wherein an increased level of cleavage compared to a control diagnoses the respiratory condition.

The invention also provides a method for diagnosing (the presence or absence of) a respiratory condition in a test sample by detecting cleavage activity of an enzyme capable of cleaving a substrate, the method comprising:
(i) bringing an indicator molecule into contact with the test sample, said indicator molecule comprising
   (a) a cleavage region comprising at least one cleavage site, which can be cleaved by said enzyme if said enzyme cleavage activity is present; and
   (b) a capture site
wherein cleavage of the at least one cleavage site produces at least two parts of the cleavage region, at least one part of which remains connected to the capture site;
(ii) adding to the test sample binding molecules capable of binding to the part of the indicator molecule containing the at least one part of the cleavage region connected to the capture site, wherein the binding molecules are incapable of binding to the indicator molecule unless and until cleavage has occurred;
(iii) capturing the part of the indicator molecule containing the at least one part of the cleavage region connected to the capture site at a capture zone through binding of capture molecules in the capture zone to the capture site; and
(iv) detecting cleavage of the at least one cleavage site by determining binding of the binding molecules to the part of the indicator molecule captured in the capture zone, wherein an increased level of cleavage compared to a control diagnoses the respiratory condition.

In specific embodiments, the respiratory condition is an inflammatory respiratory condition.

In specific embodiments, the respiratory condition is chronic obstructive pulmonary disease or inflammation of the respiratory tract (in particular the lungs) as a result of cystic fibrosis. The inventors have shown herein that the devices and methods of the invention can usefully be applied to measure elevated cleavage activity as an indicator of a respiratory condition. In order to take into account background levels of cleavage activity, the methods involve comparing measured levels of cleavage in the test sample to a control. Typically, the control represents corresponding levels of cleavage activity in a healthy subject. By "healthy subject" is meant a subject not suffering from the respiratory condition. The control may be in a corresponding test sample taken from a matched healthy control. Alternatively, the control may be a threshold level of cleavage set by determining cleavage activity in a range of healthy and diseased patients. Suitable methods for setting a threshold are well known to those skilled in the art. The threshold may be mathematically derived from a training set of patient data. The score threshold thus separates the test samples according to presence or absence of the respiratory condition. The interpretation of this quantity, i.e. the cut-off threshold may be derived in a development or training phase from a set of patients with known outcome. The threshold may therefore be fixed prior to performance of the claimed methods from training data by methods known to those skilled in the art.

The enzyme detection devices of the invention may be supplied in a format ready for immediate use. Alternatively, the essential components may be provided as a kit of parts, optionally together with suitable reagents and/or instructions for assembly of the enzyme detection device. Accordingly, in another aspect, the invention provides an enzyme detection kit for detecting the presence in a test sample of cleavage activity of an enzyme capable of cleaving a substrate, the kit comprising:
(i) an indicator molecule for adding to the test sample, said indicator molecule comprising
(a) a cleavage region comprising at least one cleavage site, which can be cleaved by said enzyme if said enzyme cleavage activity is present; and
(b) a capture site;
wherein cleavage of the at least one cleavage site produces a novel binding site;
(ii) capture molecules capable of binding to the capture site of the indicator molecule
(iii) a solid support to which the capture molecules can be attached (i.e. are attachable or attached) to form a capture zone to receive the test sample; and
(iv) binding molecules capable of binding to the novel binding site, wherein the binding molecules are incapable of binding to the indicator molecule unless and until cleavage has occurred.

In another aspect, the invention provides an enzyme detection kit for detecting the presence in a test sample of cleavage activity of an enzyme capable of cleaving a substrate, the kit comprising:
(i) an indicator molecule for adding to the test sample, said indicator molecule comprising
  (a) a cleavage region comprising at least one cleavage site, which can be cleaved by said enzyme if said enzyme cleavage activity is present; and
  (b) a capture site;
wherein cleavage of the at least one cleavage site produces at least two parts of the cleavage region, at least one part of which remains connected to the capture site;
(ii) capture molecules capable of binding to the capture site of the indicator molecule,
(iii) a solid support to which the capture molecules can be attached (i.e. are attachable or attached) to form a capture zone to receive the test sample; and
(iii) binding molecules capable of binding to the part of the indicator molecule containing the at least one part of the cleavage region connected to the capture site, wherein the binding molecules are incapable of binding to the indicator molecule unless and until cleavage has occurred.

In related aspects, the invention also provides for use of an enzyme detection device as described and defined herein for diagnosing a respiratory condition in a test sample. Similarly, the invention also provides for use of a method as described and defined herein for diagnosing a respiratory condition in a test sample. The invention further provides for use of an enzyme detection kit as described and defined herein for diagnosing a respiratory condition in a test sample. In each of these uses, the respiratory condition may be chronic obstructive pulmonary disease or inflammation of the respiratory tract as a result of cystic fibrosis.

Thus, central to many of the aspects of the invention is the indicator molecule. The indicator molecule comprises a cleavage region comprising at least one cleavage site. The cleavage site is cleaved by any enzyme or enzymes in a test sample with the relevant enzyme cleavage activity. The cleavage region provides a suitable context for the cleavage site to ensure cleavage is efficient, if the enzyme is present in the sample. In specific embodiments the cleavage region is a peptide. In addition to the peptide bond representing a protease cleavage site, the additional amino acids in the peptide may ensure specificity and sensitivity of cleavage. The cleavage region may contain multiple cleavage sites in certain embodiments, particularly where the indicator molecule is structurally constrained, for example where it also comprises a scaffold molecule.

The indicator molecule also comprises a capture site (intended to encompass at least one capture site). The capture site is a discrete region of the indicator molecule which permits immobilization of the indicator molecule, whether cleaved or uncleaved, at a capture zone. The capture site is discussed herein below in greater detail.

The indicator molecule also optionally comprises a scaffold molecule, as discussed in greater detail below.

Cleavage of the indicator molecule splits the indicator molecule to reveal or form at least one novel binding site. The two parts of the cleavage region are thus separated from one another at the site of cleavage. Typically the novel binding site comprises a conformational epitope produced as a consequence of cleavage. Use of binding molecules that bind specifically to the newly revealed binding site or sites but not to the indicator molecule prior to cleavage enables specific and sensitive detection of cleavage activity of an enzyme. Accordingly, in some embodiments, cleavage of the at least one cleavage site produces at least two parts of the indicator molecule (or cleavage region of the indicator molecule), at least one part of which contains (or remains connected to) the capture site and as a consequence of cleavage contains a binding site for binding molecules and wherein the binding molecules are incapable of binding to the binding site unless and until cleavage has occurred. In other words, the binding site is hidden or is not formed until cleavage at the cleavage site occurs.

In some embodiments, cleavage of the at least one cleavage site produces at least two separate parts of the (cleavage region of the) indicator molecule. Thus, cleavage may produce at least two parts or fragments; one part or fragment that contains or is connected to the capture site and a separate part or fragment that does not contain, or is not connected to, the capture site. The binding molecules bind to the new binding site on the part or parts of the indicator molecule that contain or include the capture site. This permits specific detection of cleavage at the site of capture of the indicator molecule through binding to the capture molecules (i.e. binding of the binding molecules is detected in the capture zone).

However, it is not essential that cleavage (at the cleavage site) produces at least two completely separate molecules, provided that cleavage produces a novel binding site for the binding molecules and wherein the binding molecules are incapable of binding to the binding site unless and until cleavage has occurred. Thus cleavage produces two parts of the cleavage region which are separated at the cleavage site. Accordingly, in some embodiments, cleavage of the at least one cleavage site produces at least two parts of the cleavage region, at least two parts of which remain connected, either directly or indirectly (for each part), to the capture site. This is shown schematically in FIG. 16A. In specific embodiments the indicator molecule contains a further linkage or connection away from the cleavage site or outside of the cleavage region such that cleavage of the at least one cleavage site produces at least two parts of the cleavage region of the indicator molecule which remain connected to one another. This does not exclude the possibility that cleavage produces at least three fragments, at least one of which does not remain connected via the further linkage or connection. This is particularly the case where the cleavage region may comprise more than one cleavage site. This is shown schematically in FIG. 16B. The further linkage or connection may comprise a disulphide bond in some embodiments. It has been found that use of scaffold molecules, linked to the indicator molecule, provides a further linkage or connection within the indicator molecules. Such scaffold molecules may act as a structural constraint that is useful for developing binding molecules that bind to the indicator molecule only after cleavage has occurred. Without being bound by theory, the structural constraint is believed to assist in producing a specific and reproducible binding site that is not present unless and until cleavage at the cleavage site has occurred. The scaffold molecule may enhance the differences in spatial conformation between the indicator molecule pre- and post-cleavage, as discussed in greater detail herein. The scaffold may also constrain the cleaved indicator molecule in a particular spatial conformation following cleavage. This may assist in improving specificity of detection in terms of the binding molecules discriminating between cleaved and uncleaved indicator molecules, by providing a clearly defined and different molecule after cleavage against which binding molecules can be designed or raised. Thus, in some embodiments, the binding molecules bind to the region of cleavage. In specific embodiments, the binding site may thus encompass both sides of the cleavage site following cleavage (i.e. at least two parts of the cleavage region). The binding molecules may bind to both parts of the indicator molecule following cleavage.

The invention therefore also provides an indicator molecule for use in detecting the presence in a test sample of cleavage activity of an enzyme capable of cleaving a substrate, the indicator molecule comprising:
(a) a cleavage region comprising at least one cleavage site, which can be cleaved by said enzyme if said enzyme cleavage activity is present,
(b) a capture site; and
(c) a scaffold molecule which acts to connect at least two parts of the indicator molecule outside of the cleavage site, such as outside of the cleavage region
wherein the scaffold further acts to structurally constrain the indicator molecule in a manner such that cleavage of the at least one cleavage site produces a novel binding site to which binding molecules bind, but wherein the binding molecules are incapable of binding to the indicator molecule unless and until cleavage has occurred.

The invention also provides an indicator molecule for use in detecting the presence in a test sample of cleavage activity of an enzyme capable of cleaving a substrate, the indicator molecule comprising:
(a) a cleavage region comprising at least one cleavage site, which can be cleaved by said enzyme if said enzyme cleavage activity is present to produce at least two parts of the cleavage region,
(b) a capture site; and
(c) a scaffold molecule which acts to connect at least two parts of the indicator molecule such that cleavage of the at least one cleavage site produces at least two parts of the cleavage region of the indicator molecule which remain connected to one another
wherein the scaffold further acts to structurally constrain the indicator molecule in a manner such that cleavage of the at least one cleavage site produces a (novel) binding site to which binding molecules bind, but wherein the binding molecules are incapable of binding to the indicator molecule unless and until cleavage has occurred.

The scaffold molecule is typically attached to the indicator molecule away from the cleavage site so that cleavage activity of the enzyme is not inhibited by the scaffold. Thus the cleavage region may be separated from the scaffold molecule by one or more linker or spacer regions. Those linker or spacer regions may incorporate the capture site in some embodiments. The scaffold molecule is typically linked to the indicator molecule by two linkages, although it is possible that additional linkages can be employed—for example 3, 4, 5 or 6 etc.—linkages depending upon the scaffold molecule that is used and the nature of the indicator molecule. It is also possible that a single scaffold molecule can be linked to multiple indicator molecules. In embodiments where the scaffold molecules contain more than two halogen substituents, in particular bromomethyl substituents, such as 4 or 6 bromomethyl substituents the scaffold molecule may provide a structural constraint for multiple indicator molecules. Each pair of substituents may be attached to connect at least two parts of a cleavage region. Thus, the scaffold effectively links (and structurally constrains) multiple separate cleavage regions. In specific embodiments, the indicator molecules comprise more than one constrained peptide (cleavage region). The cleavage regions can also be different resulting in a single molecule containing different cleavable sequences. Here it may be possible to detect cleavage of each individual peptide cleavage region using two or more distinct binding molecules (e.g. antibodies raised against its cleaved substrate). Consequently where an assay signal is required only when two or more proteases are present it is possible that binding molecule (antibody) binding only takes place when all the distinct cleavage sites have been cleaved. In this instance the binding molecule (antibody) would have to be raised to the form of indicator molecule after cleavage by the two or more proteases.

The scaffold molecule assists in constraining the cleaved ends or parts of the indicator molecule (usually a peptide) to produce a novel and specific binding site for a binding molecule (usually an antibody binding to a newly revealed or produced epitope, in particular a conformational epitope). The binding molecule may, therefore, bind specifically to either cleaved end or part of the indicator molecule or to both sides of the cleavage site (i.e. within the cleavage region either side of the cleavage site). In specific embodiments, the scaffold further acts to structurally constrain the indicator molecule in a manner such that cleavage of the at least one cleavage site produces a binding site containing both parts of the cleavage region of the indicator molecule to which binding molecules bind, but wherein the binding molecules are incapable of binding to the indicator molecule unless and until cleavage has occurred. In specific embodiments, the binding site includes the cleavage site. In specific embodiments, the binding site represents a novel structural conformation of the indicator molecule. Cleavage may produce at least one new conformational epitope. The novel binding site for the binding molecule may comprise any part of the indicator molecule, provided that enzyme cleavage activity and capture are not substantially impeded. In certain embodiments, the binding site comprises at least a portion of the cleavage region. In specific embodiments, the binding site comprises at least a portion of the scaffold molecule.

In most embodiments, the cleavage site is specific for cleavage by a protease. However, as discussed herein, the indicator molecules of the invention may be cleaved by other enzymes such as oxidoreductases, hydrolases and lyases, and include the subcategories of protease, peptidase, lipase, nuclease, carbohydrase, phosphatase, sulphatase, neuraminidase, esterase, DNAse, and RNAse. In certain embodiments, the cleavage site is specific for cleavage by an endopeptidase. One or more different proteases may be detected according to the invention. In certain embodiments, the cleavage site is specific for cleavage by a matrix metalloproteinase (MMP). This is particularly of relevance for the diagnostic applications of the invention including detection in urine samples. MMPs are zinc-dependent endopeptidases. They are responsible for cleaving various proteins, including extracellular matrix proteins. The MMPs include MMP1, MMP2, MMP3, MMP7, MMP8, MMP9, MMP10, MMP11, MMP12, MMP13, MMP14, MMP15, MMP16, MMP17, MMP19, MMP20, MMP21, MMP23A, MMP23B, MMP24, MMP25, MMP26, MMP27 and MMP28. In other embodiments, the cleavage site is specific for an elastase, such as (human) neutrophil elastase (HNE). In some embodiments, there may be a cleavage site for multiple proteases, such as multiple MMPs and/or one or more MMPs together with HNE. A suitable HNE substrate comprises, consists essentially of or consists of the following amino acid sequence:

(SEQ ID NO: 3)
CQESIRLPGC

This substrate forms a separate aspect of the invention. The substrate may contain additional residues to facilitate immobilisation such as a tyrosine residue to provide phenyl groups for attachment. In particular, the substrate may contain additional amino acid residues excluding cysteine residues so that alternative immobilisation chemistries can be used. Thus, the substrate may comprise the following amino acid sequence:

(SEQ ID NO: 4)
YCQESIRLPGC

The at least one cleavage site may be biased for cleavage by specific proteases in some embodiments. This permits the invention to be utilised in order to detect specific protease activity in the test sample. Many proteases are known and their sites of preferred cleavage well reported. In certain embodiments, the at least one cleavage site is biased for cleavage by specific matrix metalloproteinases. More specifically, in some embodiments, the at least one cleavage site is biased for cleavage by MMP-13 and/or MMP-9. The at least one cleavage site may be biased for cleavage by MMP-13, 9, 2, 12 and 8. The bias may be for the group of MMPs equally or may be in that particular order of preference. As is shown herein, it is possible to design specific indicator molecules and cleavage sites within the indicator molecules that are biased for cleavage by these particular MMPs, in the specified order of preference. Accordingly, in some embodiments, the cleavage site is within the amino acid sequence GPQGIFGQ (SEQ ID NO: 1). This may be considered a specific example of the "cleavage region" of the indicator molecule. In those embodiments, cleavage produces a part of the cleavage region of the indicator molecule containing the amino acid sequence GPQG and a part of the cleavage region of the indicator molecule containing the amino acid sequence IFQG. Either part can be the part connected to the capture site. In specific embodiments, the indicator molecule comprises the amino acid sequence CGPQGIFGQC (SEQ ID NO: 2). Inclusion of the cysteine residues provides thiol groups which represent a convenient linkage point for various scaffold molecules. The cleavage region may be separated from the attachment points for the scaffold molecule by one or more linker or spacer regions in some embodiments. Thus, the indicator molecule may comprise the structure:

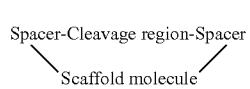

The capture site may be found within one or both of the spacers in some embodiments. Thus, the indicator molecules of the invention may comprise suitable amino acids at or near the N and C terminus to facilitate linkage to the scaffold molecule. The amino acids may comprise thiol groups. Suitable residues include cysteine and selenium. The scaffold molecules may be attached to the indicator molecules via thioether linkages.

A range of suitable scaffold molecules and methods for linking the scaffold molecules to a peptide are discussed in WO2004/077062 and WO2008/013454, the relevant disclosures of which are hereby incorporated by reference. The present invention applies these scaffold molecules in a new manner to present cleavage sites and produce new binding sites after cleavage which permit detection of enzyme cleavage activity (especially protease activity) in a test sample.

In certain embodiments, the scaffold molecule comprises a (hetero)aromatic molecule. In more specific embodiments, the (hetero)aromatic molecule comprises at least two benzylic halogen substitutents. The scaffold molecule is a halomethylarene in some embodiments, such as a halomethylarene selected from the group consisting of bis(bromomethyl)benzene, tris(bromomethyl)benzene and tetra (bromomethyl)benzene, or a derivative thereof. In specific embodiments, the scaffold is selected from the group consisting of ortho-, meta- and para-dihaloxylene and 1,2,4,5 tetra halodurene, such as meta-1,3-bis(bromomethyl)benzene (m-T2), ortho-1,2-bis(bromomethyl)benzene (o-T2), para-1,4-bis(bromomethyl)benzene (p-T2), meta-1,3-bis (bromomethyl)pyridine (m-P2), 2,4,6-tris(bromomethyl) mesitylene (T3), meta-1,3-bis(bromomethyl)-5-azidobenzene (m-T3-N3) and/or 1,2,4,5 tetrabromodurene (T4).

Suitable derivatives of halomethyl arenes include ortho, meta and para bis(bromomethyl) benzenes. More specifically 1,2-bis(bromomethyl) benzene, 1,3-bis(bromomethyl) benzene and 1,4-bis(bromomethyl) benzene. Further substituted halomethylarenes include 1,3,5-tris(bromomethyl) benzene, 1,2,4,5-tetrakis(bromomethyl)benzene and 1,2,3,4, 5,6-hexakis(bromomethyl)benzene. Polycyclic halomethylarenes include 2,7-bis(bromomethyl)-naphthalene, 1,4-bis(bromomethyl)-naphthalene, 1,8-bis(bromomethyl)-naphthalene, 1,3-bis(bromomethyl)-naphthalene, 1,2-bis(bromomethyl)-naphthalene, 2,3-bis(bromomethyl)-naphthalene, 2,6-bis(bromomethyl)-naphthalene, 1,2,3,4-tetrakis(bromomethyl)-naphthalene, 9,10-bis(bromomethyl)-phenanthrene, 5,10-bis(bromomethyl)-anthracene, and 1-(bromomethyl)-3-[3-(bromomethyl) benzyl]benzene. Methyl substituted halomethylarenes include 1,3-bis(bromomethyl)-5-methylbenzene, 2,5-bis (bromomethyl)-1,3-dimethylbenzene, 2,5-bis(bromomethyl)-1,4-dimethylbenzene, 2,4-bis(bromomethyl)-1,3,5-trimethylbenzene and 3,6-bis(bromomethyl)durene. Nitro substituted halomethylarenes include 3,4-bis(bromomethyl)-nitrobenzene and 2,3-bis(bromomethyl)-nitrobenzene. Hydroxy substituted halomethylarenes include 1,3-bis (bromomethyl)-5-hydroxybenzene and cyano substituted halomethylarenes include 2,6-bis(bromomethyl)-benzonitrile. Methoxy substituted halomethylarenes include 1,3-bis (bromomethyl)-5-methoxybenzene, 1,3-bis(bromomethyl)-2-methoxy-5-methylbenzene, 1,3-bis(bromomethyl)-5-hydroxybenzene, 2,3-bis(bromomethyl)-1,4-dimethoxybenzene, and 2,5-bis(bromomethyl)-1,4-dimethoxybenzene.

Some suitable scaffold molecules for use in the indicator molecules of the invention are shown in FIG. 14. A number of specific suitable scaffold molecules are also shown, together with proposed nomenclature, in FIG. 15.

Due to their relative rigidity and ease of synthetic use, the halomethyl arene derivatives are preferred candidates to act as scaffold molecules in the present invention. They are particularly convenient for creating constrained peptide substrates. However one can envisage other appropriate chemistries with which to "cyclise" the indicator molecule, such as a peptide. In the case of peptides containing thiols (eg: in the form of cysteine), a simple disulphide bond formation or a diepoxide derivative can be used to affect covalent closure of the structure. Another appropriate chemistry includes the "click chemistry" method, involving the cycloaddition reaction between azides and alkynes forming stable triazoles. Here for example a peptide bearing two azido lysine amino acids could be intramolecularly cross linked by a dialkyne reagent. Such reactions can be catalysed by copper. However in some examples such as those where a strained alkyne is used, no catalyst is required. A further chemical route includes that of stable hydrazone formation. Indicator molecules (in particular peptides) containing two phenyl hydrazine moieties may be cross linked intramolecularly via a dialdehyde reagent. A further chemical route is possible through peptide-based indicator molecules containing two tyrosine amino acids. These peptides can be intramolecularly crosslinked using a bis(diazo) scaffold to form the corresponding diazo adduct.

The scaffold molecules may also include further functionalities or reactive groups to facilitate generation of a novel binding site following enzymatic cleavage of the cleavage site. Thus, following cleavage at the cleavage site there are at least two parts of the cleavage region of the indicator molecule which are no longer connected to one another through the cleavage site. One or more of those "free" parts may become further constrained by interaction with the scaffold molecule. This may produce a significant change in structure of the overall molecule. This in turn permits specific binding molecules to be generated which will not cross-react with the indicator molecule prior to cleavage. Thus, by way of example, in the case of peptides constrained by a scaffold molecule one can envisage a specific conformational change after cleavage of the cleavage site. The afforded degrees of freedom in the peptide chain may allow it to self-assemble via non covalent interactions in a new stable conformation, creating a new conformational epitope unique to the molecule and recognised by the binding molecule (such as an antibody raised against the cleaved substrate). These non-covalent interactions may comprise hydrophobic interactions between the amino acid side chains and the aromatic rings in the scaffold molecule. The non-covalent interactions can be further enhanced in scaffolds with extended substitution patterns such that for example a negatively charged nitro substituent can interact with positively charged amino acids such as lysine, arginine or histidine included within the cleavage region. Hydrogen bond interactions are also possible between methoxy and/or hydroxyl aryl substituents and a number of amino acids, including serine, threonine and tyrosine. In addition the two cleaved peptide parts of the cleavage region may be free to self-assemble with each other inducing a secondary structure such as a helix or beta stranded structure after cleavage. In further embodiments, a combination of both peptide-peptide interactions and peptide-scaffold interactions, as described above, may produce a novel binding site recognised by a binding molecule. Such interactions serve to differentiate the structure in 3 dimensional space between its uncleaved "closed" form and its "open" form following cleavage and hence significantly enhance the specificity of interaction between the cleaved indicator molecule and the binding molecule (e.g. an antibody raised against the cleaved peptide product). The resulting high specificity of interaction is beneficial to the sensitivity of detection of enzyme cleavage activity within the sample because it facilitates use of the indicator molecule in excess without the risk of the binding molecule binding to uncleaved indicator molecule (e.g. the antibody raised against the cleaved peptide from binding to the uncleaved peptide).

The scaffold should not prevent cleavage at the one or more cleavage sites. In some embodiments, the scaffold may orientate the (cleavage region of the) indicator molecule to optimise or improve efficiency of cleavage at the cleavage site. The scaffold may effectively fix or constrain the cleavage region to present the cleavage site in a favourable manner for the enzyme activity to be detected. The effect of the scaffold molecule on cleavage of any given substrate can readily be tested by a simple time course experiment. A test may determine whether cleavage occurs in the presence of the enzyme within a reasonable time (e.g. 5-10 minutes). This testing can be qualified, for example through mass spec analysis, optionally in combination with HPLC as it should evolve a new hydrolysed molecule (with a different molecular mass) which should also retain differently on a reverse phase analytical column. Those indicator molecules incorporating a scaffold molecule can, for example, then be prepared as an immunogen in its purified cleaved form. This can be used to raise antibodies in a suitable animal such as a sheep, either as free peptide or conjugated to a carrier protein. Antisera may then be characterised by ELISA to immobilised antigen and an antigen column may be used to affinity purify and refine the polyclonal response specifically to the cleaved indicator molecule. The complete indicator molecule may then be tested according to the methods of the invention.

A specific indicator molecule of the invention is shown in Figure and comprises the amino acid sequence of SEQ ID NO: 3 or SEQ ID NO: 4 in which the thiol groups of the cysteine residues are used to cyclise the peptide via linkage to a halomethylarene group. Thus, an indicator molecule of the invention may comprise the structure set forth as formula I below (and shown in FIG. 23).

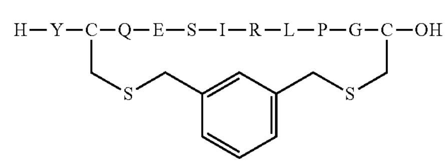

(I)

The cleaved version is shown in formula II below (and also shown in FIG. 23).

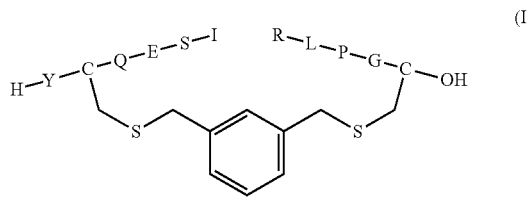

In some embodiments, the indicator molecule lacks the tyrosine residue shown in formulas I and II. This tyrosine residue is not required for HNE activity.

A range of suitable binding molecules for use in the invention are disclosed herein, which discussion applies mutatis mutandis here. Typically, the binding molecule comprises an antibody.

For the avoidance of doubt, these indicator molecules may be employed in any of the other aspects of the invention (devices, kits, methods, uses etc.).

In the context of the invention as a whole, the one or more cleavage sites may be any site at which an enzymatically-cleavable bond is present. For example, this bond may be present between neighbouring residues of the indicator molecule. Such residues may be selected from nucleotides, monosaccharides, and amino acids. The indicator molecule typically comprises a peptide cleavage region. Thus, in some embodiments, the cleavage region comprises a sequence of amino acids. In a preferred embodiment of the invention, the cleavage site is a specific peptide bond located between two amino acid residues.

In further embodiments of the invention, the at least one cleavage site is located within a peptide, a protein, a carbohydrate, a lipid or a nucleic acid cleavage region. In certain embodiments, the indicator molecule may be engineered such that it comprises the enzyme's natural substrate or a portion thereof, such that the enzyme is presented with its native cleavage site, optionally in its native state within the cleavage region. In certain other embodiments, the indicator molecule may be engineered such that it comprises an artificial or non-native cleavage site and/or substrate region. For example, the cleavage site in the indicator molecule may be engineered or mutated such that the rate of cleavage activity or specificity of cleavage activity exhibited by the enzyme is increased (or decreased) relative to the rate and/or specificity of cleavage activity of the enzyme measured under comparable conditions against the enzyme's natural substrate.

In certain embodiments of the invention, the cleavage region may comprise multiple cleavage sites, wherein cleavage at any one of the sites produces at least two parts of the cleavage region, at least one part of which remains connected to the capture site. In the context of the present invention, the term 'multiple' means at least two, at least three, at least four, and so forth. In certain embodiments, the cleavage region of the indicator molecule includes between 2, 3, 4, 5 and 10, 11, 12, 13, 14, 15, 16, 17, 18, 19, 20, 25, 50, 100, 500 or 1000 cleavage sites. In some embodiments, the indicator molecule includes between 2 and 5, 6, 7, 8, 9 or 10 cleavage sites.

In one embodiment, the multiple cleavage sites may all be identical. In this configuration, the repeated cleavage site may be relatively non-specific or may be highly specific for one enzyme or enzyme subtype as defined above. Moreover, use of an indicator molecule of this type may help to increase the sensitivity of the enzyme detection device by providing a means to increase the concentration of cleavage sites present within the test sample.

In other embodiments, the cleavage region of the indicator molecule may comprise multiple cleavage sites wherein there are at least two different cleavage sites present within the same indicator molecule. In preferred embodiments of the invention, the indicator molecule may comprise at least three, at least four, at least five, and up to at least 8 different cleavage sites.

In a further preferred embodiment, the different cleavage sites are recognised by different enzymes or different categories, subcategories or subtypes of enzymes as defined above, such that the device of the invention can be used to detect the activity of multiple different enzymes. The activities may be grouped, such that the detection of enzyme activity gives a useful result. For example, a group of enzymes may be involved in a disease state such that detection of the relevant activity of one or more of the enzyme group is diagnostically useful.

Use of multiple cleavage sites (whether identical or non-identical) may be particularly useful for situations in which very low levels of enzyme activity are to be detected in a test sample. For example, an indicator molecule having multiple cleavage sites as defined above may be used to detect enzyme activity in a urine sample containing low levels of protease. Use of multiple cleavage sites may also be particularly applicable where the indicator molecule incorporates a scaffold molecule.

In addition to a cleavage region containing at least one cleavage site, the indicator molecule comprises a capture site. The capture site mediates binding of the indicator molecule to a capture molecule present within a capture zone. Thus, the capture site is the portion of the indicator molecule responsible for retaining or localising the indicator molecule within the capture zone. Following cleavage of the indicator molecule, the capture site may remain intact or substantially intact, such that the site is still recognised and bound by a capture molecule present within the capture zone of the device. Under these circumstances, both intact indicator molecules and the part of the indicator molecules comprising the capture site following cleavage will be bound to capture molecules within the capture zone. The capture site may comprise any suitable molecule, for example a biotin molecule. It is also possible for the scaffold molecule to form a part, or the entirety, of the capture site in order to permit immobilization of the indicator molecule at a capture zone. For example, the capture zone may comprise antibodies raised against the scaffold molecule, preferably in the form as attached to the indicator molecule. In these embodiments, the scaffold molecule is not substantially involved in binding to the binding molecules. Key to effectiveness of the indicator molecules is immobilization via the interaction between capture site and capture molecules at the capture zone and simultaneous binding by binding molecules after cleavage has occurred. In those embodiments in which the scaffold molecule defines a part of the binding site for the binding molecules after cleavage, the capture site must be sufficiently distinct to prevent either or both binding events from being impeded.

As noted above, the cleavage site may be within a peptide, a protein, a carbohydrate, a lipid or a nucleic acid cleavage region. In specific embodiments of the invention, the cleavage region and capture site are defined by discrete amino acids or groups of amino acids within a peptide or protein.

As used herein the term "peptide" is intended to mean a length of amino acids of no more than (about) 20, 30, 40 or 50 amino acids.

Alternatively, the capture site may be present in a region of the indicator molecule which is separate to the region in which the cleavage site is located. Thus, in certain embodiments of the invention, the capture site may be present within a capture region, and the cleavage site may be present within a separate cleavage region of the indicator molecule. In embodiments wherein the capture site is in a separate region of the indicator molecule to the cleavage site, the capture site may comprise materials or residues entirely distinct from those found in the region of the molecule containing the cleavage site. For example, the cleavage region may comprise amino acid residues whilst the capture site may comprise or consist of a biotin moiety. Moreover, in embodiments wherein the indicator molecule comprises separate regions bearing the cleavage site and capture site, said regions may be associated by any means known to one of skill in the art. In a preferred embodiment, said regions may be associated via a direct covalent linkage. Said regions may be immediately adjacent or may be separated by a linker or spacer, for example, a polyethylene glycol moiety.

The enzyme or enzymes to be detected according to the invention must be capable of cleaving the indicator molecule at the cleavage site. This activity is required in order for the indicator molecule to be cleaved at the cleavage site, to produce at least two parts of the cleavage region of the indicator molecule, at least one part of which remains connected to the capture site. Thus, in some embodiments of the present invention, the enzyme or enzymes to be detected are selected from the following categories:—oxidoreductases, hydrolases and lyases, and include the sub-categories of protease, peptidase, lipase, nuclease, carbohydrase, phosphatase, sulphatase, neuraminidase, esterase, DNAse, and RNAse. In specific embodiments, the enzyme is a protease. In certain embodiments, the protease comprises an endopeptidase. One or more different proteases may be detected according to the invention. In certain embodiments, the protease is a matrix metalloproteinase (MMP). MMPs are zinc-dependent endopeptidases. They are responsible for cleaving various proteins, including extracellular matrix proteins. The MMPs include MMP1, MMP2, MMP3, MMP7, MMP8, MMP9, MMP10, MMP11, MMP12, MMP13, MMP14, MMP15, MMP16, MMP17, MMP19, MMP20, MMP21, MMP23A, MMP23B, MMP24, MMP25, MMP26, MMP27 and MMP28. In other embodiments, the cleavage site is specific for an elastase, such as (human) neutrophil elastase (HNE). In some embodiments, there may be a cleavage site for multiple proteases, such as multiple MMPs and/or one or more MMPs together with HNE. A suitable HNE substrate comprises, consists essentially of or consists of the amino acid sequence of SEQ ID NO: 3 or SEQ ID NO: 4 and may be incorporated into an indicator molecule, such as shown in formula I or II (including forms lacking the tyrosine residue).

As discussed herein, the at least one cleavage site may be biased for cleavage by specific proteases in some embodiments. This permits the invention to be utilised in order to detect specific protease activity in the test sample. Many proteases are known and their sites of preferred cleavage well reported. In certain embodiments, the at least one cleavage site is biased for cleavage by specific matrix metalloproteinases. More specifically, in some embodiments, the at least one cleavage site is biased for cleavage by MMP-13 and/or MMP-9. The at least one cleavage site may be biased for cleavage by MMP-13, 9, 2, 12 and 8. The bias may be for the group of MMPs equally or may be in that particular order of preference. As is shown herein, it is possible to design specific indicator molecules and cleavage sites within the indicator molecules that are biased for cleavage by these particular MMPs, in the specified order of preference. Accordingly, in some embodiments, the cleavage site is within the amino acid sequence GPQGIFGQ (SEQ ID NO: 1), which thus forms the cleavage region. In those embodiments, cleavage produces a part of the indicator molecule containing the amino acid sequence GPQG and a part of the indicator molecule containing the amino acid sequence IFQG. Either part can be the part containing the capture site. As is shown herein, the inventors have produced binding molecules which specifically recognise either resultant sequence, but not the original (pre-cleavage) amino acid sequence.

Within the context of the present invention the indicator molecules (via the capture site) may bind to the capture molecules with relatively high affinity. In some embodiments, the dissociation constant ($k_d$) for the indicator molecule will be relatively low and preferably between 0M and $1\times10^{-7}$M (depending on the sensitivity required of the assay). In certain embodiments of the invention, the dissociation constant for the indicator molecule will be between $1\times10^{-15}$M and $1\times10^{-9}$M.

In certain embodiments of the invention, such a binding interaction may be achieved as a result of direct binding of the capture site of the indicator molecule to the capture molecule present in the capture zone. In this context, direct binding means binding of the indicator molecule (via the capture site) to the capture molecule without any intermediary.

In some embodiments of the invention, the capture site of the indicator molecule and the capture molecule present in the capture zone are two halves of a binding pair. In this context, a binding pair consists of two molecules or entities capable of binding to each other. In certain embodiments of the invention, the binding interaction is specific such that each member of the binding pair is only able to bind its respective partner, or a limited number of binding partners. Moreover, as detailed above, it is preferable for the binding pair to exhibit relatively high affinity. The binding pair may be a binding pair found in nature or an artificially generated pair of interacting molecules or entities.

In some embodiments of the invention, the capture site of the indicator molecule and the capture molecule are two halves of a binding pair wherein the binding pair is selected from the following:—an antigen and an antibody or antigen binding fragment thereof; biotin and avidin, streptavidin, neutravidin or captavidin; an immunoglobulin (or appropriate domain thereof) and protein A or G; a carbohydrate and a lectin; complementary nucleotide sequences; a ligand and a receptor molecule; a hormone and hormone binding protein; an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.

In particular embodiments of the invention, the binding pair consists of biotin and streptavidin. In a further embodiment of the invention, the capture site of the indicator molecule comprises an epitope and the capture molecule comprises an antibody, which specifically binds to the epitope present at the first capture site. In the context of the present invention, the term antibody covers native immunoglobulins from any species, chimeric antibodies, humanised antibodies, F(ab')$_2$ fragments, Fab fragments, Fv fragments, sFv fragments and highly related molecules such as those based upon antibody domains which retain specific binding affinity (for example, single domain antibodies). The antibodies may be monoclonal or polyclonal. Thus, in specific embodiments, the capture molecule comprises an antibody. In other embodiments, the capture site comprises a biotin molecule and the capture zone comprises a streptavidin molecule.

In certain embodiments of the invention, binding of the capture site of the indicator molecule to the capture molecule of the device may be indirect. In the context of the present invention, "indirect binding" means binding mediated by some intermediate entity capable of bridging the capture site of the indicator molecule and the capture molecule, for example an "adaptor" capable of simultaneously binding the capture site of the indicator molecule and the capture molecule.

Wherein binding of the indicator molecule to the capture molecule is indirect and mediated by an adaptor, it may be possible for a plurality of indicator molecules to bind to each capture molecule. In this context, a plurality means at least two, at least three, at least four, and so forth. This may be achieved by the incorporation of a multivalent adaptor molecule, for example, a streptavidin molecule capable of simultaneous binding to multiple biotin-containing indicator molecules in addition to a capture molecule consisting of or comprising biotin.

Embodiments of the device wherein a plurality of indicator molecules bind to each capture molecule, may be used to achieve improved assay accuracy as described in greater detail herein.

Another key molecule to the invention is the binding molecule. The invention relies upon binding molecules capable of binding to the novel binding site produced on cleavage, or the part of the indicator molecule containing the capture site following cleavage, wherein the binding molecules are incapable of binding to the indicator molecule unless and until cleavage has occurred. Thus, in specific embodiments, the binding molecule comprises an antibody. For the avoidance of doubt, the term antibody covers native immunoglobulins from any species, chimeric antibodies, humanised antibodies, F(ab')$_2$ fragments, Fab fragments, Fv fragments, sFv fragments and highly related molecules such as those based upon antibody domains which retain specific binding affinity (for example, single domain antibodies). The antibodies may be monoclonal or polyclonal. The inventors have produced antibodies which recognise the cleavage region only after cleavage and will therefore not bind to the indicator molecule (to any significant degree) unless and until cleavage at the cleavage site has occurred. Antibodies may be produced according to techniques known in the art. This may rely upon immunisation of an animal, such as a sheep, rabbit or goat, with the cleavage products. For example immunisation may be performed using the part of the cleavage region which remains connected to the capture site after cleavage, optionally including the capture site itself. Polyclonal antibodies may be isolated from serum and affinity purified. Monoclonal antibodies may be produced using well-known and characterised hybridoma technology.

Thus, the invention also provides a binding molecule, typically an antibody, which binds to an indicator molecule as defined herein after cleavage. The invention provides a binding molecule, typically an antibody, which binds to a novel binding site in the indicator molecule produced as a result of cleavage wherein the binding molecule is incapable of binding to the indicator molecule unless and until cleavage has occurred. In some embodiments, the binding molecule binds in the cleavage region. In specific embodiments, cleavage of the at least one cleavage site produces at least two parts of the cleavage region of the indicator molecule, at least one part of which remains connected to the capture site and as a consequence of cleavage contains a binding site for binding molecules and wherein the binding molecules are incapable of binding to the binding site unless and until cleavage has occurred. In some embodiments, cleavage of the at least one cleavage site produces two separate parts of the indicator molecule and thus the binding molecule binds to one or both of the separate parts following cleavage. In agreement with this, the invention provides a binding molecule, optionally an antibody, which binds to an indicator molecule comprising the amino acid sequence GPQG but not to an indicator molecule comprising the amino acid sequence GPQGIFGQ (SEQ ID NO: 1) (as the cleavage region). Similarly, the invention provides a binding molecule, optionally an antibody, which binds to an indicator molecule comprising the amino acid sequence IFGQ but not to an indicator molecule comprising the amino acid sequence GPQGIFGQ (SEQ ID NO: 1) (as the cleavage region). The invention further provides a binding molecule, optionally an antibody, which binds to an indicator molecule comprising the amino acid sequence of SEQ ID NO: 3 or SEQ ID NO: 4 only when cleaved, in particular cleaved between the isoleucine and arginine residue (i.e. not to the amino acid sequence prior to cleavage). The indicator molecule may be constrained by attachment to a scaffold molecule as discussed herein. An example is shown in FIG. 23.

In those embodiments of the invention in which the indicator molecule is structurally constrained and in which cleavage of the at least one cleavage site produces at least two parts of the cleavage region of the indicator molecule which remain connected to one another, the binding molecules may bind to the cleavage region following cleavage. In specific embodiments, the binding molecules bind to both parts of the cleavage region of the indicator molecule following cleavage. Thus, the binding molecules may bind a region that effectively spans the cleavage site following cleavage. Structural constraint of the indicator molecule, for example using the scaffold molecules as discussed herein, provides a well-defined and stable binding site for the binding molecules following cleavage. In specific embodiments, the binding site to which the binding molecule binds represents a novel structural conformation of the indicator molecule. Cleavage may produce at least one new conformational epitope. The binding site for the binding molecule may comprise any part of the indicator molecule. This may be with the proviso that enzyme cleavage activity and/or capture of the indicator molecule are not substantially impeded by binding of the binding molecule. In certain embodiments, the binding site comprises at least a portion of the cleavage region and/or at least a portion of the linker or spacer region to which the scaffold molecule is attached and which separates the scaffold molecule from the cleavage region. In other embodiments, the binding molecule may bind to a novel binding site that comprises at least a portion of the scaffold molecule.

The binding molecule may be directly or indirectly labelled with a reporter molecule to permit detection of binding of the binding molecule to the indicator molecule. The reporter molecule may be any substance or moiety suitable for detection by any means available to those skilled in the art. Thus, the reporter molecule is typically capable of signal generation or production. In certain embodiments of the invention, the reporter molecule is selected from the following:—a gold particle; a chromogen; a luminescent compound; a fluorescent molecule; a radioactive compound; a visible compound; a liposome or other vesicle containing signal producing substances; an electroactive species; or a combination of enzyme and its substrate. A suitable enzyme-substrate combination for use as a reporter moiety may be the enzyme alkaline phosphatase and the substrate nitro blue tetrazolium-5-bromo-4-chloro-3-indolyl phosphate. In a particular embodiment of the invention, the reporter moiety is a gold particle.

Indirect labelling of the binding molecules with a reporter molecule is also envisaged within the present invention. Thus, the reporter molecule may be attached to a further binding molecule which in turn binds to the binding molecule to provide the label. This indirect binding may be mediated by an adaptor capable of simultaneously binding the binding molecule and the reporter molecule. As an illustrative embodiment, where the binding molecule is an antibody, indirect labelling could be mediated by a further antibody that binds to the antibody binding molecule in specific fashion. The further antibody may be directly labelled with a reporter molecule such as a gold particle; a chromogen; a luminescent compound; a fluorescent molecule; a radioactive compound; a visible compound; a liposome or other vesicle containing signal producing substances; an electroactive species; or a combination of enzyme and its substrate. A suitable enzyme-substrate combination for use as a reporter moiety may be the enzyme alkaline phosphatase and the substrate nitro blue tetrazolium-5-bromo-4-chloro-3-indolyl phosphate. In a particular embodiment of the invention, the reporter moiety is a gold particle.

In embodiments of the invention wherein the reporter molecule binds to the binding molecule by virtue of an adaptor molecule, the adaptor may be pre-complexed with the binding molecule prior to the addition of the test sample to the indicator molecule, provided that the adaptor does not prevent binding of the binding molecule to the cleaved indicator molecule.

The adaptor may be any material or molecule capable of mediating the indirect interaction of the binding molecule with the reporter molecule. In some embodiments, the adaptor is streptavidin and the binding molecule comprises a biotin molecule. The adaptor may also be an "adaptor binding pair" wherein said binding pair comprises:
(i) a first member capable of binding to the binding molecule; and
(ii) a second member capable of binding to the first member of the pair and to the reporter molecule. In certain embodiments of the invention, the detection region of the indicator molecule comprises biotin, the first member of the adaptor binding pair is avidin or streptavidin, the second member of the adaptor binding pair is biotin, and the reporter molecule comprises a moiety capable of binding biotin.

The inclusion of an adaptor molecule or an adaptor binding pair may facilitate the binding of multiple reporter molecules to each binding molecule. For example, the use of multivalent streptavidin as the adaptor will allow for simultaneous binding of both a biotin-containing binding molecule in addition to multiple biotin-containing reporter molecules.

The invention may be performed in lateral flow or vertical flow devices in certain embodiments. Generally, therefore, the invention relies upon some form of solid support. The solid support may define a liquid flow path for the sample. In specific embodiments, the solid support comprises a chromatographic medium or a capillary flow device. The invention may be provided in a test strip format in some embodiments. A representative example is shown in FIG. 2 and described in further detail herein.

In specific embodiments of the invention, the capture zone is formed on a solid support. Any support to which the capture molecules may be attached to form a capture zone is intended to be encompassed. The solid support may take the form of a bead (e.g. a sepharose or agarose bead) or a well (e.g. in a microplate) for example. Thus, in certain embodiments the device comprises a solid support to which the capture molecules are attached to form the capture zone. In the case of the kits of the invention, the solid support may be provided without the capture molecules attached. In those embodiments, the user of the kit may immobilize the capture molecules on the solid support to form the capture zone prior to use of the device with a test sample. The kit may, therefore, also comprise means for immobilizing the capture molecules on the solid support. The immobilizing means may comprise any suitable reagents to permit the capture zone to be formed. The solid support may be pre-formed with suitable immobilizing means. For example, the solid support may comprise biotin molecules arranged to interact with avidin (e.g. streptavidin) molecules that form (part of) the capture molecules. Of course, other binding pair interactions may be used to immobilize the capture molecules on the solid support to form a capture zone, as discussed herein and as would be readily understood by one skilled in the art.

The capture zone may be defined by the immobilization therein or thereon of capture molecules capable of binding to the capture site of indicator molecules. Immobilization of capture molecules may be achieved by any suitable means. Wherein the device is a flow device comprising a chromatographic medium, the capture molecules may be immobilized by directly binding to the medium or immobilized indirectly via binding to a carrier molecule, such as a protein, associated with, or bound to, the medium.

In further embodiments, the solid support further comprises a sample application zone to which the sample is applied. The sample application zone may be pre-loaded with the indicator molecule, such that when the test sample is applied any enzyme in the sample acts upon the cleavage site of the indicator molecule within the sample application zone. The sample application zone may contain a barrier, which holds the sample in the sample application zone for a pre-determined period of time. This permits the sample to interact with the indicator molecule for a sufficient period to achieve measurable levels of cleavage. This may be 1, 2, 3, 4, 5, 6, 7, 8, 9, 10, 15, 20, 30, 60 minutes or more depending upon the enzyme to be detected, as would be readily understood by one skilled in the art. The barrier may be degraded by the sample, or otherwise removed, after this period of time thus allowing the sample to continue to flow through the device. Alternatively, the test sample and indicator molecule may be pre-mixed or pre-incubated prior to adding the mixture to the device, such as to the sample application zone. However, where the test sample and indicator molecule may be pre-mixed or pre-incubated it is possible to omit the sample application zone. Here, it may be possible to add the mixture directly to the capture zone to permit immobilization of the indicator molecules through interaction with the capture molecules. In some embodiments, the test sample may be applied to the chromatographic medium at a site upstream from the capture zone such that it is drawn, for example by capillary action, through the capture zone. The chromatographic medium may be made from any material through which a fluid is capable of passing, such as a fluidic channel or porous membrane. In certain embodiments of the invention, the chromatographic medium comprises a strip or membrane, for example a nitrocellulose strip or membrane.

The binding molecules must be provided in the device in a manner that permits interaction with the indicator molecule, if cleaved at the cleavage site. The binding molecules may, therefore, be pre-mixed with the indicator molecules prior to application to the device. This may be before or after the indicator molecules have been mixed with the test sample. It is preferably after to avoid any effect the binding molecules may have on enzyme activity (in the test sample) at the cleavage site of the indicator molecule. The binding molecules can also be provided on or in the device at any point upstream of the capture zone, such that the binding molecules encounter the test sample and indicator molecules before the indicator molecules are immobilised (via interaction between the capture site of the indicator molecule and capture molecules defining the capture zone). Alternatively, the binding molecule may be added to the capture zone after the test sample and indicator molecules have been added to the capture zone. This ensures that any indicator molecule will already be immobilized at the capture zone, providing (in the case of cleaved indicator molecule) a binding site for the binding molecules to produce a signal.

Depending upon the particular enzyme cleavage activity that is being detected, it may be necessary to incorporate suitable enzyme inhibitors into the devices or methods. This may be important to prevent the enzyme from acting upon other components of the device or method, such as the binding molecules or capture molecules. Where the test sample is pre-incubated with the indicator molecule, it may be advantageous to add an inhibitor of the enzyme activity at the end of the incubation period. This is preferably before the binding molecules come into contact with the test sample. Alternatively, the enzyme activity inhibitor or inhibitors may be included in the device at any point upstream of the binding molecules, where the binding molecules are provided on or in the device. This is upstream of the capture zone (per the discussion herein above). The inhibitor may be simply dried or passively adsorbed onto the device such that the test sample mobilises the inhibitor as it passes through the device. It should be noted that use of an inhibitor is not essential. For example, some of the enzyme activities detected according to the invention such as specific protease activity may be sufficiently specific that the protease will not act on any other components of the device or method than the substrate. The cleavage sites of particular enzymes are well known in the art and can be used to design the various components of the devices and methods. For example, in silico screening may be performed (e.g. using freely available tools such as BLAST according to standard settings) to confirm that the cleavage site of the enzyme to be detected is not contained within any of the relevant molecules; such as the binding molecules and capture molecules. It is also possible to check for cross-reactivity by incubating the relevant molecules (e.g. binding molecules and capture molecules) with the enzyme activity to be tested and detecting whether cleavage occurs. In some embodiments, the relevant molecules will not be acted upon due to the nature of the enzyme cleavage activity to be detected. As an example, if a nuclease activity is being detected, this should not display any cleavage activity in relation to an antibody binding molecule or streptavidin or antibody capture molecule.

The solid support may further comprise a control zone, downstream of the capture zone in relation to sample flow, and the sample application zone if present, containing further binding molecules which bind to the binding molecules to indicate successful completion of an assay using the device. Alternatively, the further binding molecules may bind to a further molecule added to the sample or to the device and which flows with the sample through the device. The further molecule may be labelled, either directly or indirectly, with a reporter molecule as defined herein. Preferably, the reporter molecule is the same reporter molecule as attached to the binding molecules, for ease of detection, although it may be different. The control zone is spatially separated from the capture zone, for example to produce two separate test lines if the reporter is bound or immobilized in each respective zone. This control zone is used to confirm that the test sample, including the binding molecules, has passed through the entire device and confirms that the device is operating correctly. A positive signal is expected at the control zone independent of whether enzyme cleavage activity is present in the sample or not. The further binding molecules are selected based upon the nature of the binding molecules which bind to the cleavage site of the indicator molecules or on the nature of the further molecule added to the sample. The binding molecules and further binding molecules or further molecules and further binding molecules may form a binding pair as defined herein. For example, if the binding molecule is a species specific antibody (e.g. a sheep antibody), the further binding molecule may be an anti-species antibody (e.g. an anti-sheep antibody). Alternatively, if the further molecule is an antibody from a different species, e.g. a chicken or a goat, the further binding molecule may be an appropriate anti-species antibody. This permits immobilization of the binding molecule or further molecule at the control zone by virtue of a specific interaction. The further binding molecules may be immobilized in the control zone by any suitable means, for example by a covalent or non-covalent interaction.

In all aspects of the invention, the test sample may be any material known or suspected to contain an enzyme with cleavage activity. The test sample may be derived from any source. In certain embodiments, the test sample may be derived from a biological source including fluids such as blood (including serum and plasma), saliva, urine, milk, fluid from a wound, ascites fluid, peritoneal fluid, amniotic fluid and so forth. In some embodiments, the test sample is wound fluid and the device is used to detect enzyme activity, preferably protease activity, in the wound fluid as a means to assess the status and/or rate of healing of a wound. In specific embodiments, the test sample is urine and the device is used to detect the activity of enzymes, in particular proteases, in the urine. The specific diagnostic applications of the invention as discussed herein may be particularly applicable to certain representative sample types, in particular urine, saliva or sputum. In other embodiments, the sample may be an environmental sample in which cleavage activity may be desirably tested. For example, the sample may be a water, food or dust sample. In the context of food and drink samples, cleavage activity may be detected for example in relation to shelf-life of the product. Samples may also be laboratory or industrial samples, for example to test for proteases or other cleavage enzymes as contaminants. The contaminants may be found during various laboratory processes such as protein purification or in industrial processes such as fermentations.

The test sample may be collected by any suitable means and presented in any form suitable for use with the present invention, including solid or liquid forms. Moreover, as part of obtaining the test sample from its original source, the sample may undergo one or more processing or pre-treatment steps prior to testing using the invention. In one embodiment, a solid sample may be processed so as to produce a solution or suspension for testing. Moreover, in certain embodiments, the test sample may be stored, for example frozen at around −20° C., as a means of preserving the sample for any given length of time prior to testing using the invention.

It should be noted that the invention is typically performed in vitro based upon isolated samples. The methods of the invention may include steps of obtaining a sample for testing in some embodiments.

BRIEF DESCRIPTION OF THE DRAWINGS

The invention will now be described by way of example with respect to the accompanying drawings in which:

FIG. 2 is a schematic view of an enzyme detection device in accordance with the present invention and shows operation of the device in the absence (FIG. 2A) or presence (FIG. 2B) of enzyme cleavage activity.

FIG. 5 shows an example of synthesis of a structurally constrained indicator molecule.

FIG. 7 (FIGS. 7A and 7B) demonstrates the sensitivity of the assay of the invention when run with spiked MMP-9 buffer samples. The detectable limit for MMP-9 was approximately 4 ng/ml with a sample volume of 75111. FIG. 7A shows reader values across the entire concentration range of MMP-9, whereas

FIG. 11 contains graphs (FIGS. 11A and 11B) comparing the ability of a commercially available active MMP-9 assay kit and the assay of the invention to detect MMP9. FIG. 11A shows reader values across the entire concentration range of MMP-9, whereas

FIG. 14 shows a number of scaffold molecules useful in the indicator molecules described herein, together with proposed nomenclature.

FIG. 15 shows some attachment options for scaffold molecules to the indicator molecules.

FIG. 21 shows MMP9 standard curves for all combinations shown in FIG. 1.

FIG. 24 shows HPLC analysis of elastase digestion of a cyclised peptide substrate including the amino acid sequence of SEQ ID NO: 3.

FIG. 25 presents mass spectrometric data confirming that the cyclised SEQ ID NO: 3 substrate is cleaved at a single site.

DESCRIPTION OF PREFERRED EMBODIMENTS

Figure 1:
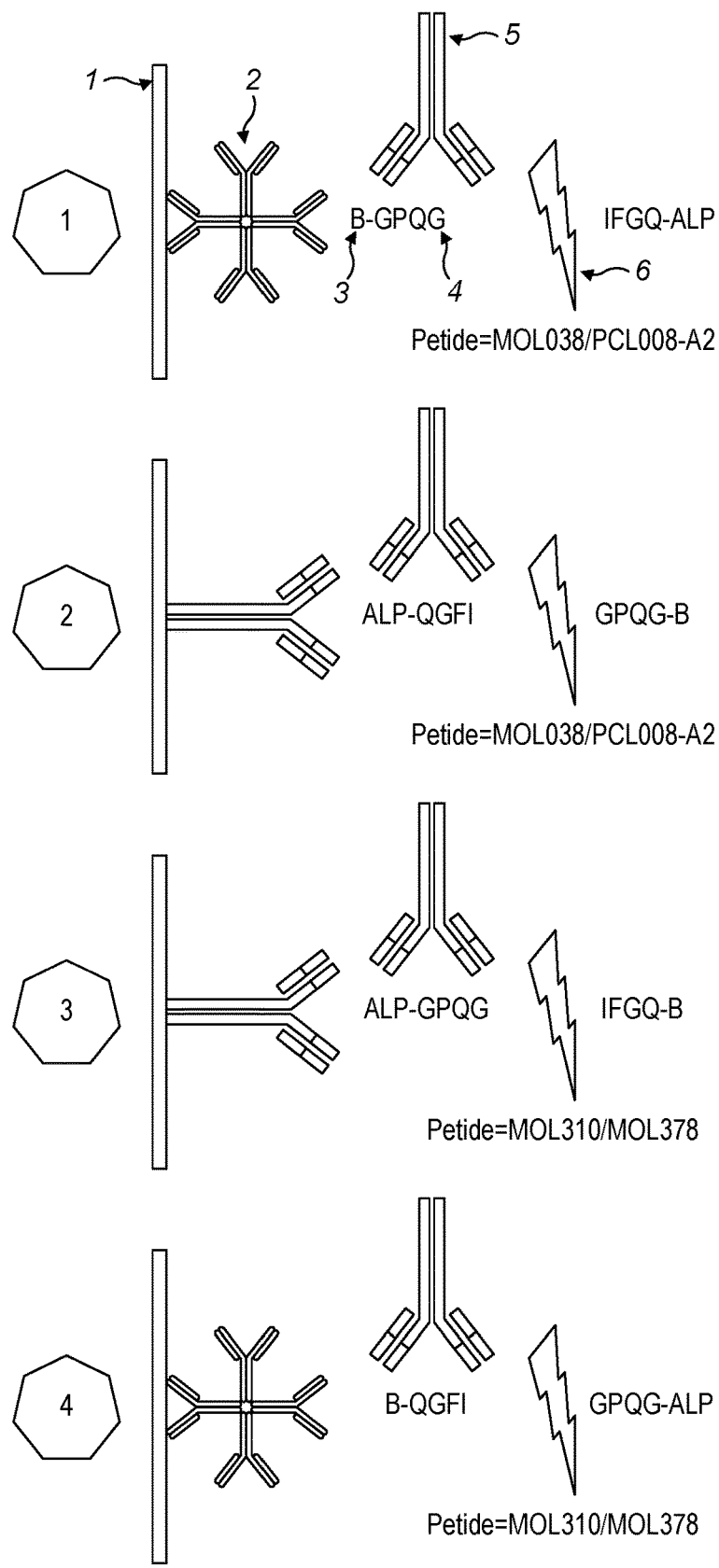
FIG. 1 is a schematic view of four different formats of the assay in accordance with the invention. Each format relies upon the same basic components of solid support (1), capture molecule (2), an indicator molecule containing a capture site (3) and a cleavage site (4) and a binding molecule (5) that binds to the indicator molecule only after cleavage (6) has occurred.

FIG. 1 is a schematic view of four different formats of the assay in accordance with the invention. Each format relies upon the same basic components of solid support (1), capture molecule (2), an indicator molecule containing a capture site (3) and a cleavage site (4) and a binding molecule (5) that binds to the indicator molecule only after cleavage (6) has occurred.

In formats 1 and 4, the capture molecule (2) is streptavidin. Here, the capture molecule (2) binds to a biotin capture site (3) within the indicator molecule. In formats 2 and 3, the capture molecule (2) is an antibody. Here, the capture molecule (2) binds to an epitope capture site (3) within the indicator molecule. The epitope is found in the alternative long peptide (ALP) which is derived from human chorionic gonadotropin (hCG).

Once the indicator molecule of the invention is added to a test sample, any enzyme specifically recognising the cleavage site (4) present, may cleave the indicator molecule (6). This cleavage event (6) produces a binding site for the specific antibody binding molecule (5). The binding molecule (5) is unable to bind to the indicator molecule until cleavage (6) has occurred. Thus, in formats 1 and 3 the antibody binding molecule (5) binds to the amino acid sequence GPQG produced as a result of cleavage of the GPQGIFGQ sequence. In formats 2 and 4, on the other hand, the antibody binding molecule (5) binds to the amino acid sequence QGFI, also produced as a result of cleavage of the GPQGIFGQ sequence. In each format, the antibody binding molecule (5) does not bind to the GPQGIFGQ sequence prior to cleavage (not shown).

FIG. 2 is a schematic view of an enzyme detection device in accordance with the present invention and shows operation of the device in the absence (FIG. 2A) or presence (FIG. 2B) of enzyme cleavage activity. The test strip includes an adhesive liner (1) upon which the other components of the device are assembled. From right to left, the sample application zone (2) is in the form of an absorbent pad. This is laid partially overlapping the conjugate pad (3), which is impregnated with the labelled binding molecules (7). In alternative embodiments, the labelled binding molecules may be impregnated in the sample application zone and this removes the need for a separate conjugate pad. The conjugate pad (3) is in fluid connection with a nitrocellulose membrane (4). The nitrocellulose membrane (4) contains immobilized streptavidin molecules (5) which define a capture zone. The membrane (4) further contains immobilized further binding molecules (6) downstream of the capture zone which bind to further labelled molecules (11) which pass through the device with the sample and form a separate control zone. Alternatively, the immobilised further binding molecules may bind to labelled binding molecules (7). The device optionally further comprises an absorbent pad (8) to absorb any test sample and reagents reaching the end of the device.

In use, the indicator molecule (9) is added to the test sample prior to bringing the test sample into contact with the sample application zone (8) of the device. As shown in FIG. 2A, in the absence of enzyme cleavage activity in the test sample, the indicator molecule (9) remains uncleaved at the cleavage site. Upon sample flow into the conjugate pad (3), the binding molecules (7) are unable to bind to the indicator molecule (9) because cleavage of the cleavage site has not occurred. The indicator molecules become bound at the capture zone via the interaction between streptavidin (5) and the biotin capture site (10) of the indicator molecule (9). The labelled binding molecules (7) are not immobilized at the capture zone because they cannot bind to the indicator molecules (9). Accordingly, the labelled binding molecules flow through to the control zone and beyond. Further labelled molecules (11) also pass through the device to the control zone where they are immobilized by binding to the immobilized further binding molecules (6). Thus, absence of enzyme cleavage activity is displayed as a signal only at the control zone, but not at the capture zone. Excess sample, potentially containing labelled binding molecules (7), flows into the absorbent pad (8).

As shown in FIG. 2B, in the presence of enzyme cleavage activity in the test sample, the indicator molecule (9) is cleaved at the cleavage site. Upon sample flow into the conjugate pad (3), the binding molecules (7) are able to bind to the indicator molecule (9) because cleavage of the cleavage site has occurred. The indicator molecules become bound at the capture zone via the interaction between streptavidin (5) and the biotin capture site (10) of the indicator molecule (9). The labelled binding molecules (7) are immobilized at the capture zone due to binding to the indicator molecules (9) at the cleavage site. Due to the relative excess of labelled binding molecule (7) to binding sites at the capture zone some labelled binding molecules (7) still flow through to the control zone and beyond. Further labelled molecules (11) also pass through the device to the control zone where they are immobilized by binding to the immobilized further binding molecules (6). Thus, presence of enzyme cleavage activity is displayed as a signal both at the capture zone and the control zone. Excess sample, potentially containing cleavage products of the indicator molecule that do not contain the biotin capture site (10), flows into the absorbent pad (8).

It should be noted that the control zone is optional. The presence or absence of enzyme cleavage activity in the sample can be monitored solely based upon the presence or absence of a corresponding signal at the capture zone.

Figure 3:
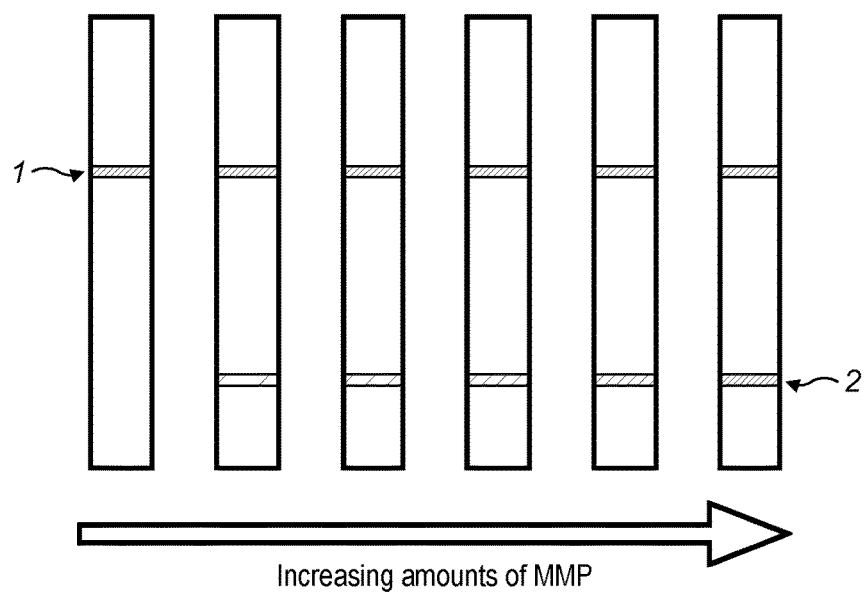
FIG. 3 shows the visual read-out of the assay (shown in FIG. 2) as levels of MMP activity in the test sample are increased.

FIG. 3 shows the visual read-out of the assay (shown in FIG. 2) as levels of MMP activity in the test sample are increased. As can readily be seen, the signal at the control zone (1) is constant as MMP amounts increase. In contrast, as MMP amounts increase, the signal at the capture zone (2) also increases. This is due to cleavage of the indicator molecule at the cleavage site by MMP activity. This reveals a binding site, enabling binding of the binding molecules which is detected at the capture zone (2) via interaction between capture molecules defining the capture zone and the capture site of the indicator molecules.

Figure 4:
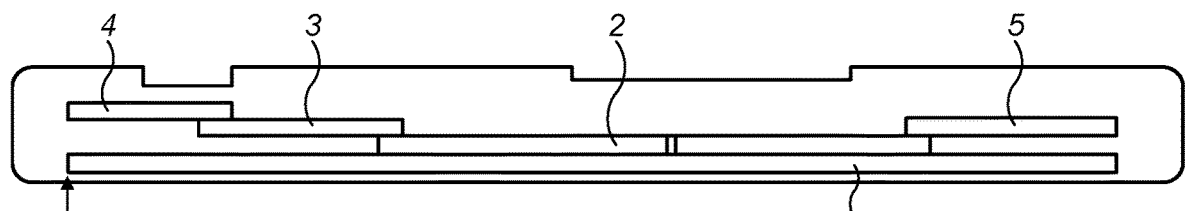
FIG. 4 is a schematic view of an enzyme detection device in accordance with the present invention. The figure specifies the exact longitudinal dimensions and position of each of the card components.

FIG. 4 is a schematic view of one specific enzyme detection device in accordance with the present invention. The table below provides a legend for the figure and specifies the exact longitudinal dimensions and position of each of the card components in this particular embodiment. Of course, the dimensions and positions may be varied as would be readily understood by one skilled in the art.

| Component | Size | Position from Datum point |
| --- | --- | --- |
| Backing card (1) | 60 mm | 0 mm |
| Nitrocellulose Membrane (2) | 25 mm | 20 mm |
| Conjugate Pad (3) | 17 mm | 5 mm |
| Sample Pad (4) | 10 mm | 0 mm |
| Absorbent Pad (5) | 22 mm | 38 mm |

FIG. 5 shows an example of synthesis of a structurally constrained indicator molecule. It should be noted that additional spacer or linker regions may be included between the cleavage region and the site of attachment of the scaffold molecule.

Figure 5A:
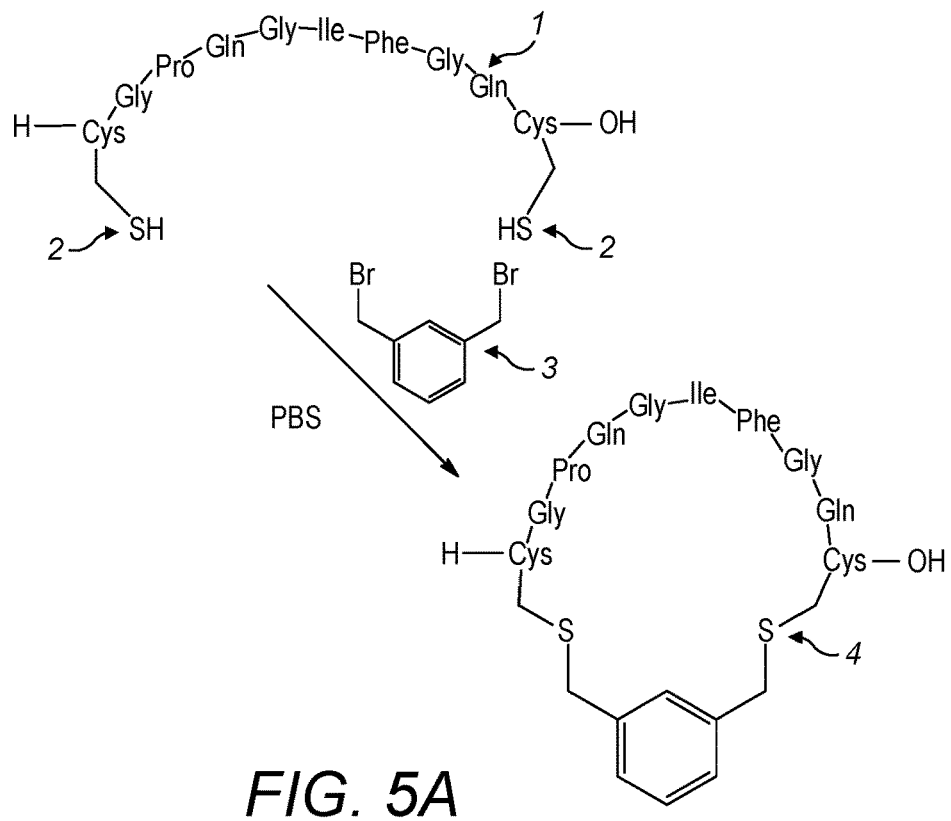
In FIG. 5A initially, a linear peptide (1) is synthesised, for example using solid phase Fmoc chemistry. The peptide may be purified for example by High Performance Liquid Chromatography (HPLC). The peptide is then constrained, or cyclised, by reaction between thiol groups on the peptide (2) and the scaffold molecule (3). This reaction produces a structurally constrained "clipped" peptide (4).

In FIG. 5A initially, a linear peptide (1) is synthesised, for example using solid phase Fmoc chemistry. The peptide may be purified for example by High Performance Liquid Chromatography (HPLC). The peptide is then constrained, or cyclised, by reaction between thiol groups on the peptide (2) and the scaffold molecule (3). This reaction produces a structurally constrained "clipped" peptide (4).

Figure 5B:
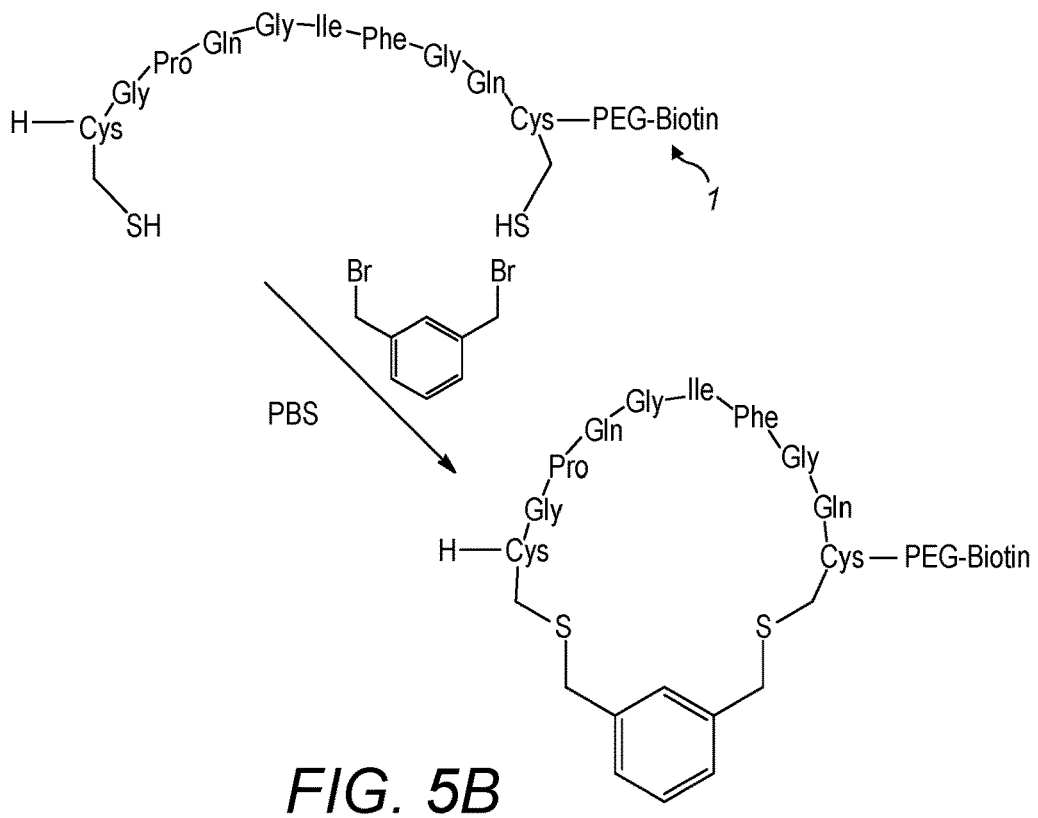
In FIG. 5B, the indicator molecule is synthesised to include the capture site (1), for example by synthesis of the linear peptide on a pre-loaded Biotin-PEG resin.

In FIG. 5B, the indicator molecule is synthesised to include the capture site (1), for example by synthesis of the linear peptide on a pre-loaded Biotin-PEG resin.

Figure 6:
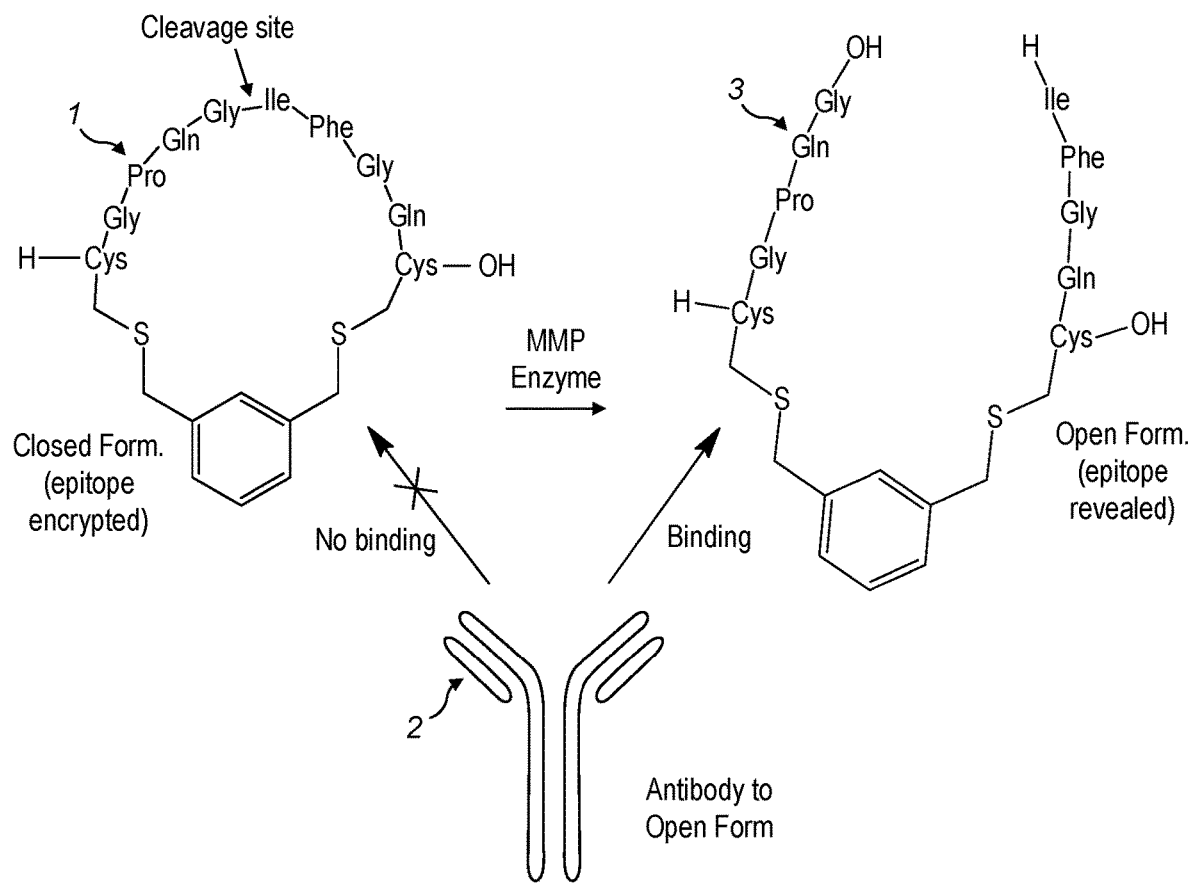
FIG. 6 shows schematically the ability of the binding molecules used in the invention to bind exclusively to the cleaved indicator molecule. In the absence of enzyme cleavage activity, the structurally constrained indicator molecule (1) is not bound by the antibody binding molecule (2). This antibody is generated using the cleaved indicator molecule (3) as antigen and thus only binds to this "open" form of the molecule.

FIG. 6 shows schematically the ability of the binding molecules used in the invention to bind exclusively to the cleaved indicator molecule. In the absence of enzyme cleavage activity, the structurally constrained indicator molecule (1) is not bound by the antibody binding molecule (2). This antibody is generated using the cleaved indicator molecule (3) as antigen and thus only binds to this "open" form of the molecule.

Figure 13:
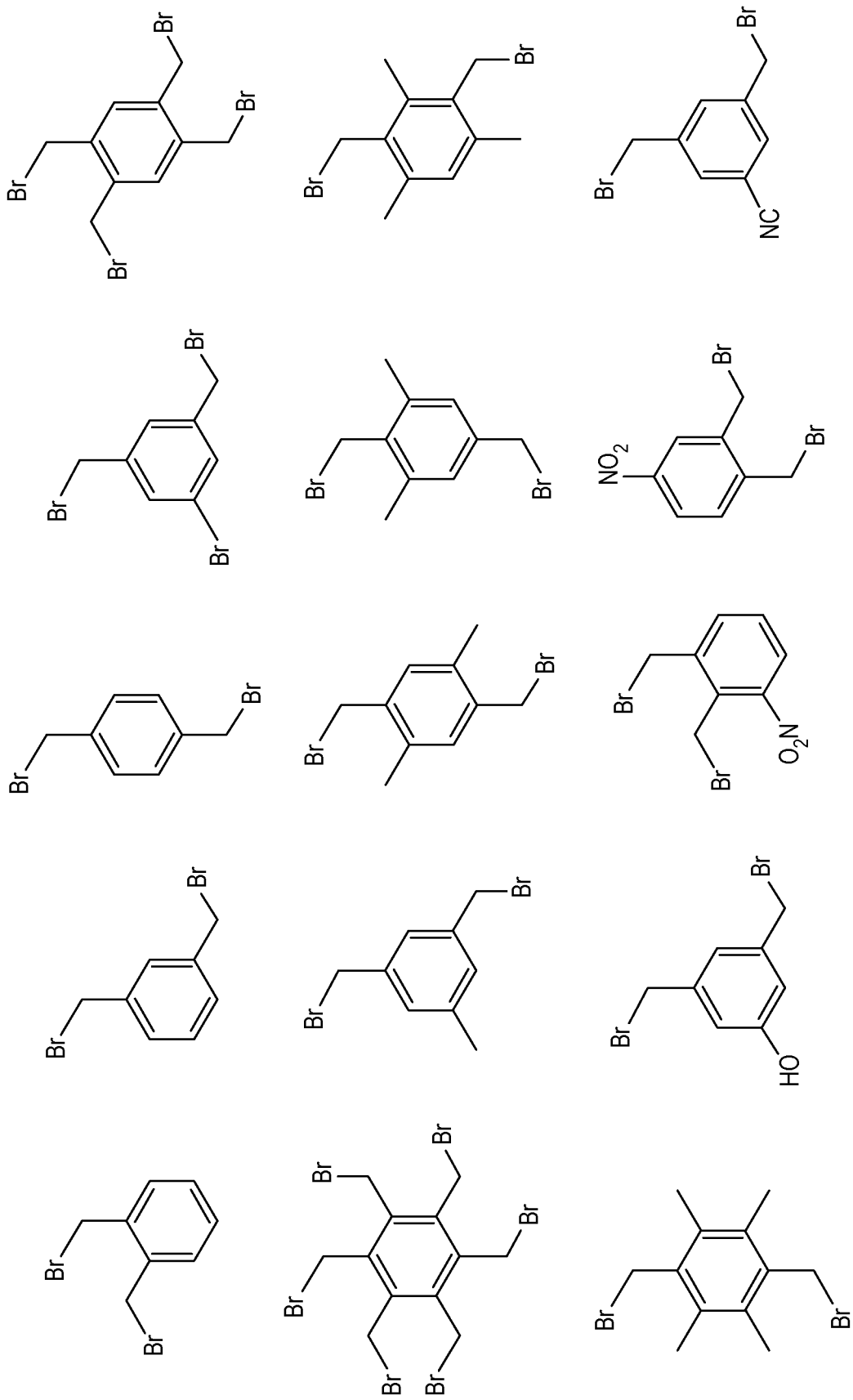
FIG. 13 shows a number of scaffold molecules useful in the indicator molecules described herein.
Figure 13:
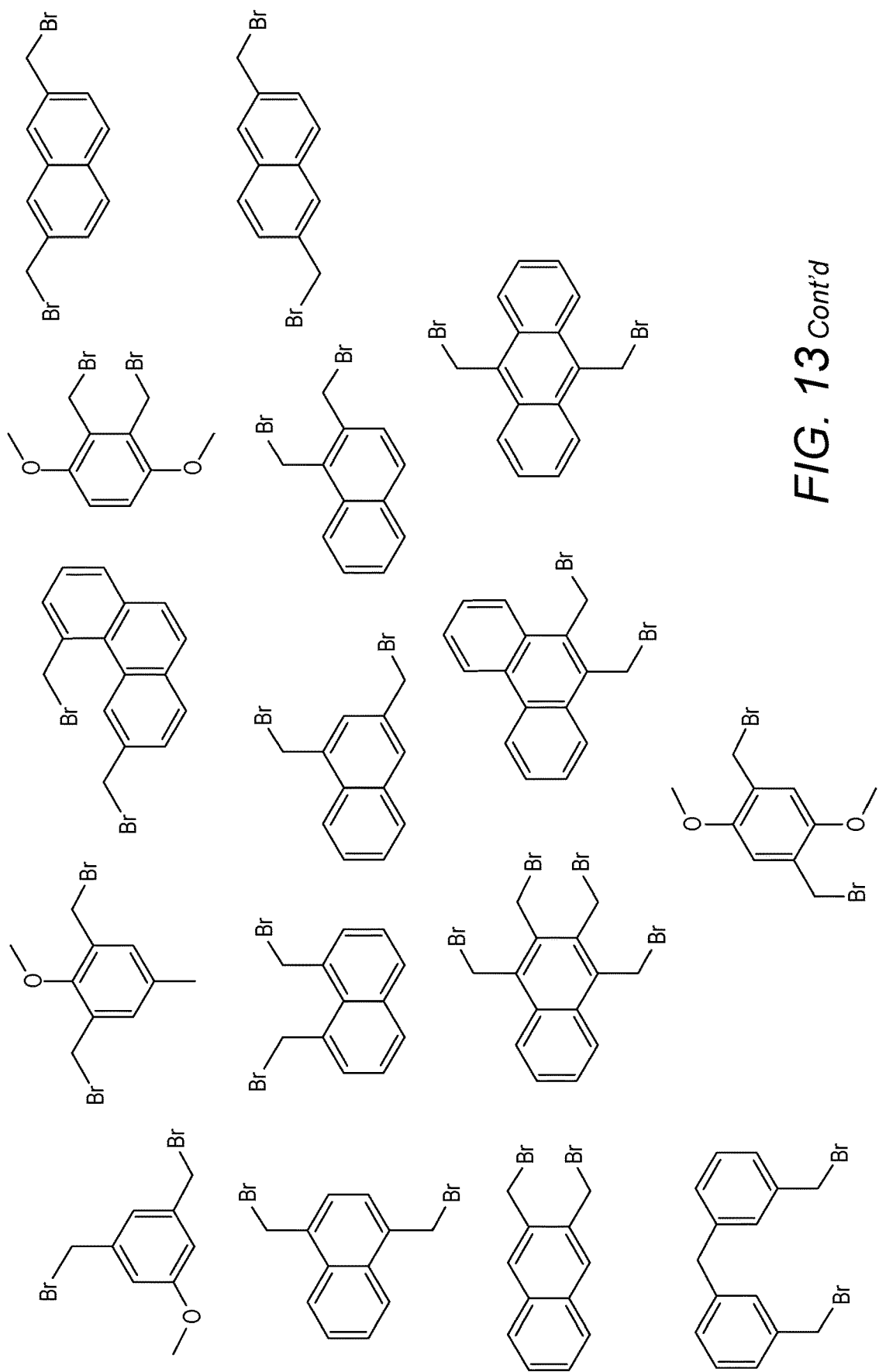

FIGS. 13 and 14 show a range of suitable scaffold molecules for use in the invention.

Figure 15A:
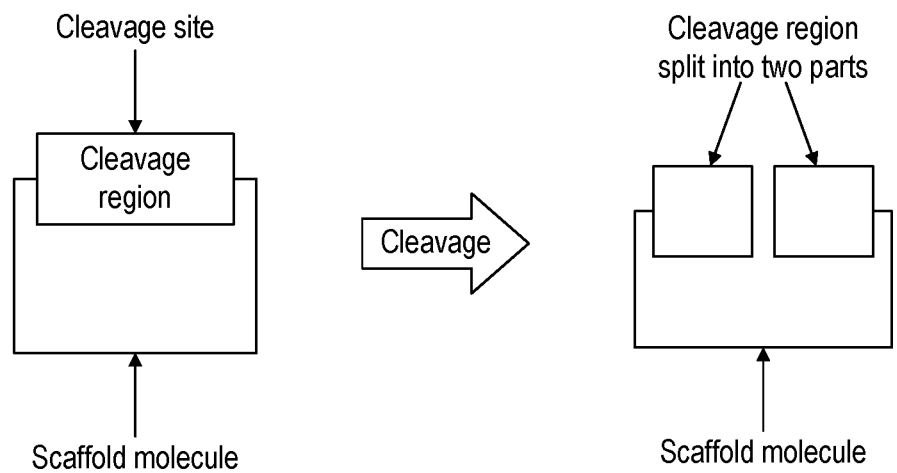
FIG. 15A shows products of cleavage at a single cleavage site and FIG. 15B shows products of cleavage at two separate cleavage sites.
Figure 15B:
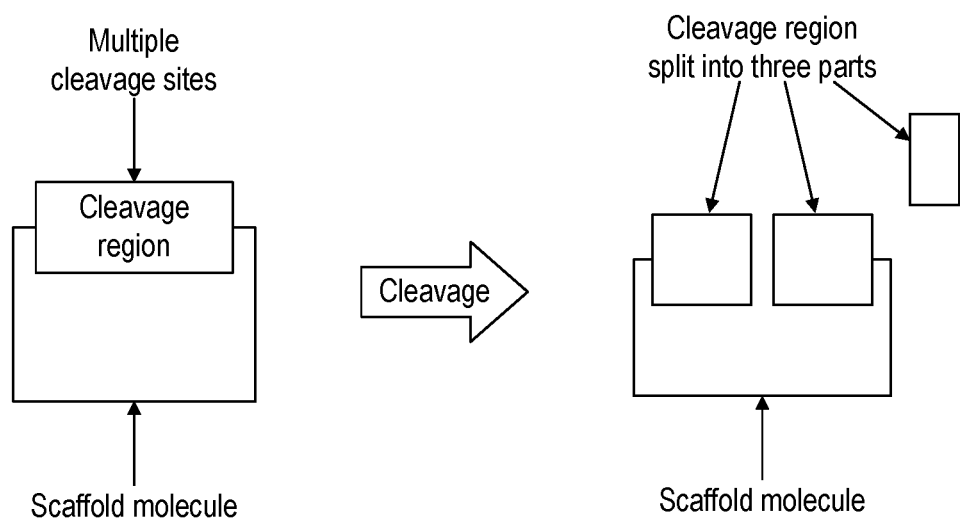

FIG. 15 shows, in schematic form, some attachment options for scaffold molecules to the indicator molecules. FIG. 15A shows products of cleavage at a single cleavage site and FIG. 15B shows products of cleavage at two separate cleavage sites.

Figure 23:
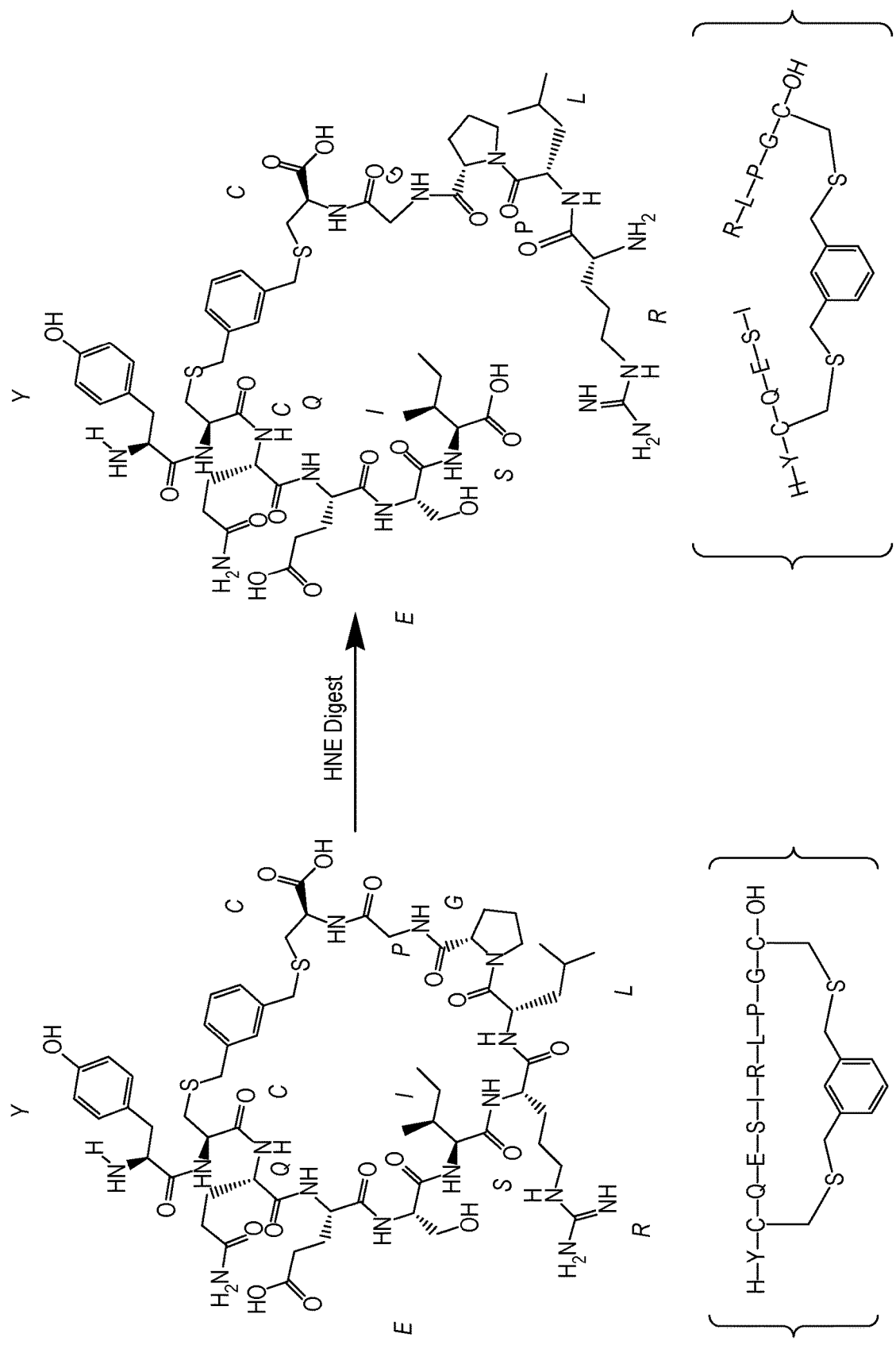
FIG. 23 shows a cyclised peptide substrate for Human Neutrophil Elastase (HNE) in both pre-digested and digested forms.

A Human Neutrophil Elastase substrate is shown in FIG. 23 in the form of an indicator molecule of the invention. Synthesis of this substrate/indicator molecule is discussed in Examples 9 and 10 below. The substrate contains the amino acid sequence CQESIRLPGC (SEQ ID NO: 3) which is cyclised using an appropriate scaffold (in this case 1,3-dibromomethylbenzene). Cyclisation utilises the thiol groups provided by the two cysteine residues to link with the scaffold. Cleavage by HNE at the peptide bond between the isoleucine and arginine residues opens up the structure to reveal a new binding site (or "cryptotope"). HNE cleaves the substrate at a single site to produce a reliable binding site. The additional tyrosine residue (see SEQ ID NO: 4) facilitates attachment to further moieties such as a carrier protein as discussed herein.

The invention will be further understood with reference to the following experimental examples.

EXAMPLES

Throughout the examples and figures the invention may be referred to as "Ultimate ELTABA".

Example 1

A Lateral Flow Platform of the Invention for Detection of Matrix Metalloprotease-9 (MMP-9)

A kit comprises the following components:—
1) A device for sample collection (e.g. for urine)
2) A lateral flow test-strip, which is mounted in a plastic case. The test strip has a capture zone comprising polystreptavidin as a first test line across the flow-path of the test strip. A second capture zone comprising anti-chicken antibodies adsorbed as a control line across the flow-path of the test strip, downstream of the test line may be included as a control line. There is an observation window in the plastic case through which to view the test and control line. There is also an integrated sample-receiving pad, upstream of the first test line. In addition, the test strip has gold particles bearing sheep antibody (CF1522) dried into the test strip, downstream of the sample-receiving pad which can be reconstituted by the addition of the sample.
3) A tube, in which the sample collection device may be placed, together with the indicating molecule.
4) An indicator molecule containing the cleavable sequence, in this example, (GPQGIFGQ) which carries a terminal biotin group connected via a polyethylene glycol spacer/linker which allows it to form a complex with the capture line, polystreptavidin.

The Test Strip

A test strip for the detection of protease activity in a sample was constructed in accordance with the present invention, as described below. The assay was based on the cleavage of the indicator molecule in the presence of various MMP's to expose an epitope visible to the Sheep antibody (CF1522) conjugated to gold particles.

The methods used were all in accordance with standard procedures well known in the art.

A. Preparation of CF1522:40 nm Gold Conjugate

Affinity purified sheep antibody CF1522 (Ig Innovations, CF1522) was conjugated to 40 nm gold particles at a concentration giving an OD of 5 at 520 nm (BBI International, GC40). The antibody was loaded at a concentration of 15 µg/ml in a 20 mM BES buffer pH 7.8. 0.2% BSA (Sigma, A7906) was used as a blocking solution to minimise non-specific binding.

B. Preparation of Gold-Impregnated Conjugate Pads

A glass fibre conjugate pad (Millipore, G041, 17 mm×300 mm) was sprayed with CF1522:40 nm gold conjugate (Mologic) at OD4, diluted in gold drying buffer (1 M Tris, 150 mM sodium chloride, 20 mM sodium Azide, 3% BSA, 5% Sucrose, 1% Tween 20 at pH 9.4) at 0.8 µl/mm with the Isoflow dispenser (15 mm spray height). The processed conjugate band was dried in a tunnel dryer at 60° C. at a speed of 5 mm/sec. The dried gold conjugate-impregnated conjugate pads were stored dried in a sealed foil pouch with desiccant at room temperature.

C. Preparation of Antibody-Impregnated Nitrocellulose Membrane

All reagents were striped on Unistart CN140 membrane (Sartorius, CN140, 25 mm×300 mm) at a dispense rate of 0.1 µl/mm. A test line polystreptavidin (BBI, Polystrep N 01041048K) at a concentration of 1 mg/ml was positioned 7 mm from base of membrane. Processed membrane was dried in a tunnel dryer at 60° C. at a speed of 10 mm/sec. The dried antibody-impregnated Nitrocellulose Membrane was stored in a sealed foil pouch with desiccant at room temperature.

D. Card Assembly

A test card was assembled according to the following procedure and in accordance with FIG. 4 which specifies the exact longitudinal dimensions and position of each of the card components.

1. A 60×300 mm piece of clear plastic film with a release liner protected adhesive, serving as the back laminate, designated 1 in FIG. 4, (G&L Precision Die Cutting, GL-48077) was placed on top of a worktable. The release liner was peeled to expose the adhesive.

2. The reaction membrane (prepared as in section C) was attached on top of the adhesive side of the back cover, 20 mm from the lower end.
3. The impregnated conjugate pad (prepared as in section B) was attached on top of the back cover with 2 mm overlap on top of the reaction membrane.
4. The sample pad (MDI, FR-1, 10×300 mm) was placed on top of the back cover with 5 mm overlap on top of the conjugate pad.
5. The absorbent pad (Gel blotting paper, Ahlstrom, grade 222, 22×300 mm) was placed on top of the upper side of the back cover with a 2 mm overlap on top of the reaction membrane.

The card was trimmed to 5 mm width strips using an automated die cutter (Kinematic, 2360) and assembled into plastic housings (Forsite). The devices were closed using a pneumatic device clamp specifically manufactured for these devices at Mologic.

The table lists the strip components and respective positioning on a backing card.

| Component | Size | Position from Datum point |
|---|---|---|
| Backing card (1) | 60 mm | 0 mm |
| Nitrocellulose Membrane (2) | 25 mm | 20 mm |
| Conjugate Pad (3) | 17 mm | 5 mm |
| Sample Pad (4) | 10 mm | 0 mm |
| Absorbent Pad (5) | 22 mm | 38 mm |

Buffer standards were produced containing different concentrations of active MMP-9 (Alere San Diego) ranging from 1000 ng/ml down to 1 ng/ml.

STEP 1: Each standard was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad which subsequently made contact with the conjugate pad and re-hydrated the dried CF1522 antibody attached to the gold particles. Intact indicator molecule was not recognised by the gold conjugate and migrated in an uncomplexed state towards the polystreptavidin test line where it was immobilised via the biotin attached to the indicator molecule. Any MMP-9 present in the sample cleaved the indicator molecule at the cleavage site, exposing the recognisable epitope thus allowing the gold conjugate to form a complex with the cleaved stub.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually and with a Forsite Lateral flow device reader. A semi-quantitative scoring system with a scale of 0-10, in which 1 was the lowest detectable colour intensity and 10 was the highest observed colour intensity was used for the visual readings.

Figure 7A:
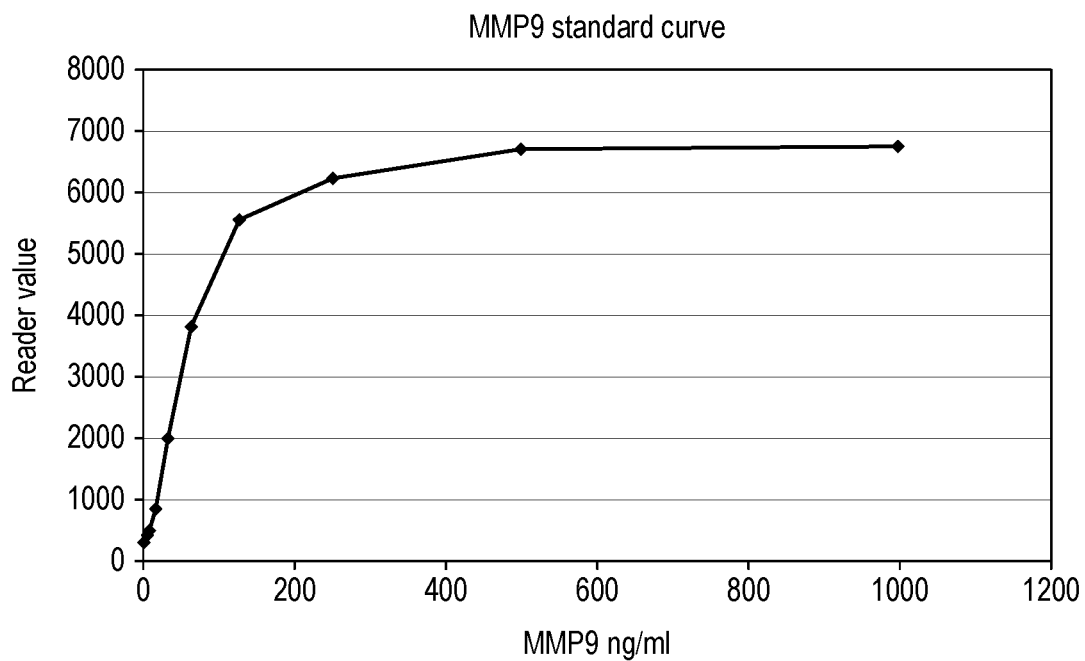
Figure 7B:
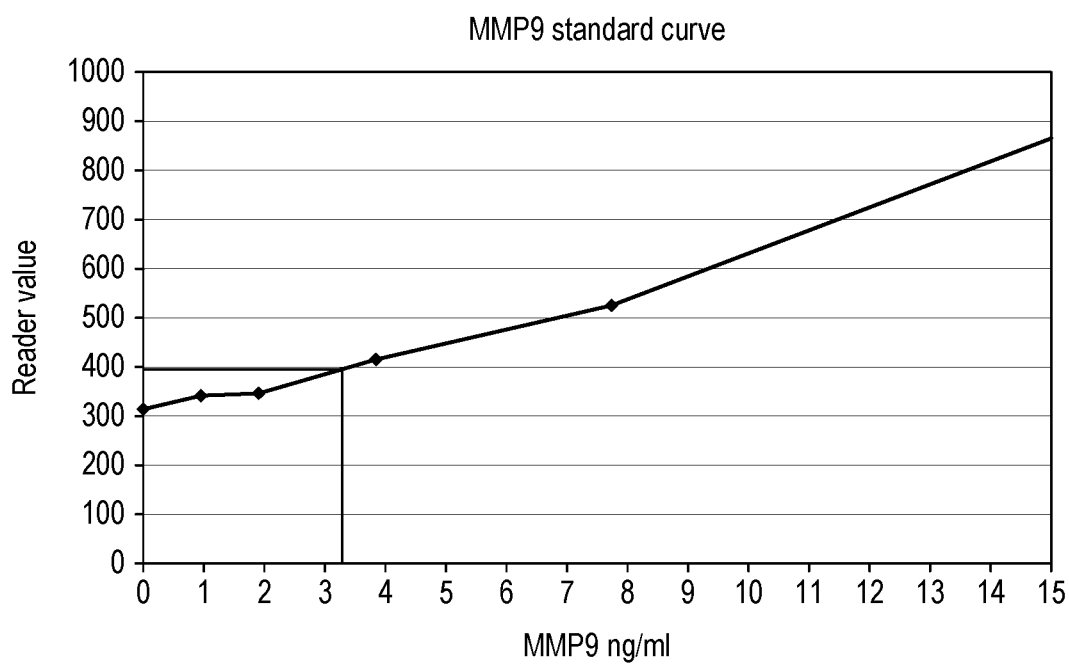
FIG. 7B is an expanded view at MMP-9 concentrations between 0 and 15 ng/ml.

FIG. 7 (FIGS. 7A and 7B) demonstrates the sensitivity of the assay when run with spiked MMP-9 buffer samples. The detectable limit for MMP-9 was approximately 4 ng/ml with a sample volume of 75 μl. FIG. 7A shows reader values across the entire concentration range of MMP-9, whereas FIG. 7B is an expanded view at MMP-9 concentrations between 0 and 15 ng/ml.

The reader units are displayed in the table below where a value above 400 was deemed a positive result:

| ng/ml MMP9 | reader value |
|---|---|
| 1000 | 6770 |
| 500 | 6729 |
| 250 | 6225 |
| 125 | 5581 |
| 62.5 | 3826 |
| 31.25 | 2029 |
| 15.625 | 882 |
| 7.8125 | 524 |
| 3.90625 | 413 |
| 1.953125 | 343 |
| 0.9765625 | 338 |
| 0 | 312 |

Example 2

Matrix Metalloprotease (MMP) Specificity of a Lateral Flow Format of the Invention The kit and test strip synthesis were performed as for Example 1.

Various MMP's (Enzo) were prepared in buffer (Aq. Solution of 50 mM Tris, 150 mM sodium chloride, 20 mM sodium azide, 1% vol/vol Tween 20, at pH 8.0) at 0.5 μg/ml.

STEP 1: Each MMP solution was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad which subsequently made contact with the conjugate pad and re-hydrated the dried CF1522 antibody attached to the gold particles. Intact indicator molecule was not recognised by the gold conjugate and migrated in an uncomplexed state towards the polystreptavidin test line where it was immobilised via the biotin attached to the indicator molecule. Any MMP-9 present in the sample cleaved the indicator molecule at the cleavage site, exposing the recognisable epitope thus allowing the gold conjugate to form a complex with the cleaved stub.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually and with a Forsite Lateral flow device reader. A semi-quantitative scoring system with a scale of 0-10, in which 1 was the lowest detectable colour intensity and 10 was the highest observed colour intensity was used for the visual readings.

Figure 8:
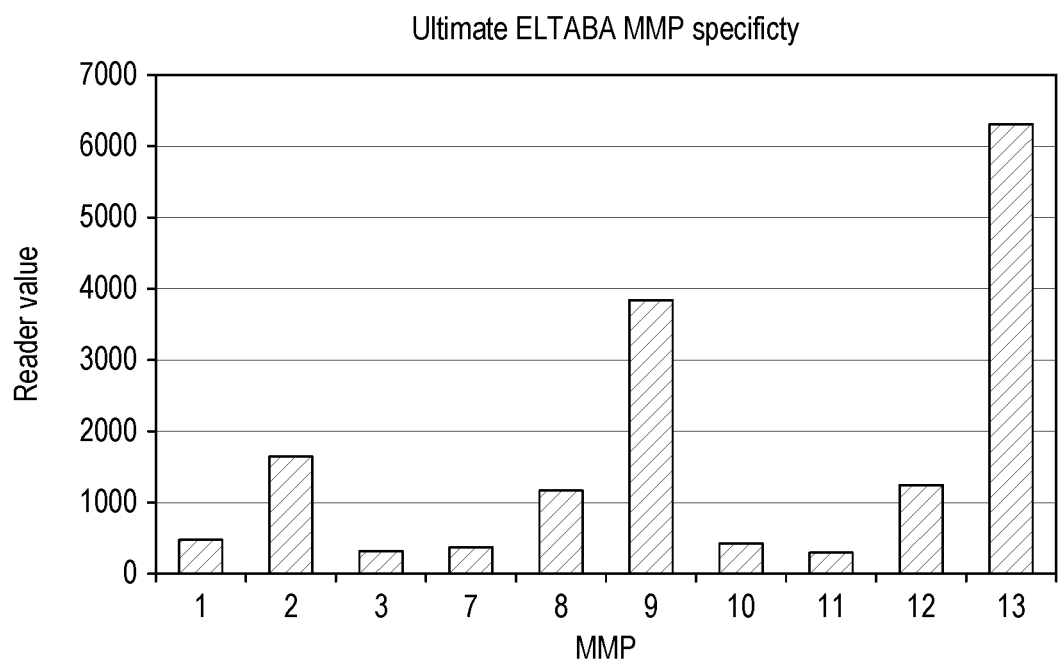
FIG. 8 demonstrates that the specific version of the assay of the invention uses a cleavable sequence that is biased towards MMP13, MMP12, MMP9, MMP8 and MMP2. Other versions of the assays of the invention may use sequences with different targets depending on the application required.

FIG. 8 demonstrates that this version of the invention uses a cleavable sequence that is biased towards MMP13, MMP12, MMP9, MMP8 and MMP2. Other versions of this invention may use sequences with different targets depending on the application required.

The table below shows the read-out values for each of the MMPs tested:

| MMP | Reader value |
|---|---|
| 1 | 477.5 |
| 2 | 1608.5 |
| 3 | 336.5 |
| 7 | 373 |
| 8 | 1140.5 |
| 9 | 3844 |
| 10 | 444 |
| 11 | 279.5 |
| 12 | 1252.5 |
| 13 | 6348.5 |

Example 3

Detection of Enzyme Activity in Urine

The kit and test strip synthesis were performed as for Example 1.

Samples were collected from healthy volunteers (9) and from patients suffering from a respiratory disease. Samples were donated from nine patients with Cystic Fibrosis (CF) and seven patients with Chronic Obstructive Pulmonary Disease (COPD) and stored at −80° C. until used.

STEP 1: Each sample was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad which subsequently made contact with the conjugate pad and re-hydrated the dried CF1522 antibody attached to the gold particles. Intact indicator molecule was not recognised by the gold conjugate and migrated in an uncomplexed state towards the polystreptavidin test line where it was immobilised via the biotin attached to the indicator molecule. Any MMP-9 present in the sample cleaved the indicator molecule at the cleavage site, exposing the recognisable epitope thus allowing the gold conjugate to form a complex with the cleaved stub.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually and with a Forsite Lateral flow device reader. A semi-quantitative scoring system with a scale of 0-10, in which 1 was the lowest detectable colour intensity and 10 was the highest observed colour intensity was used for the visual readings.

Figure 9:
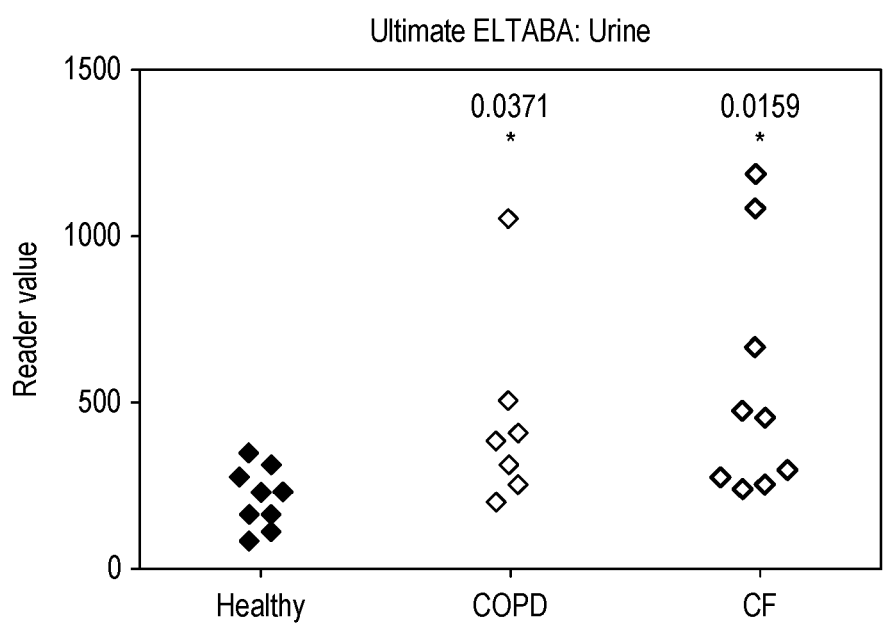
FIG. 9 demonstrates that measurable amounts of active proteases (in particular MMPs, including MMP-9) can be found in urine samples and that higher levels are present in samples obtained from patients with a respiratory disease. A significant difference was observed with COPD samples when compared to samples collected from healthy controls (P=0.03) and CF samples to healthy controls (P=0.01).

FIG. 9 demonstrates that measurable amounts of active proteases (in particular MMPs, including MMP-9) can be found in urine samples and that higher levels are present in samples obtained from patients with a respiratory disease. A significant difference was observed with COPD samples when compared to samples collected from healthy controls (P=0.03) and CF samples to healthy controls (P=0.02).

Example 4

Detection of Enzyme Activity in Wound Fluid

The kit and test strip synthesis were performed as for Example 1.

Wound samples from 18 patients were tested on the ultimate ELTABA device to measure active MMP's in this biologic matrix. The samples were extracted from a swab (Copan, 552C.US) in MMP buffer buffer (Aq. Solution of 50 mM Tris, 100 mM sodium chloride, 10 mM Calcium Chloride, 50 μM 20 mM zinc chloride, 0.025% Brij 35, 0.05% sodium azide at pH 8.0) and then frozen at −20° C. until use. The addition d a chelating agent (5 mM EDTA) determined the specificity of the device to calcium dependent enzymes e.g. MMP's.

STEP 1: Each wound sample was diluted 1 in 20 in MMP buffer and 75 μl was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad which subsequently made contact with the conjugate pad and re-hydrated the dried biotin attached to the gold particles. Intact indicator molecule was not recognised by the gold conjugate and migrated in an uncomplexed state towards the Polystreptavidin test line where it was immobilised via the biotin attached to the indicator molecule. Any MMP-9 present in the sample cleaved the indicator molecule at the cleavage site, exposing the recognisable epitope thus allowing the gold conjugate to form a complex with the cleaved stub.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually and with a Forsite Lateral flow device reader. A semi-quantitative scoring system with a scale of 0-10, in which 1 was the lowest detectable colour intensity and 10 was the highest observed colour intensity was used for the visual readings.

Figure 10:
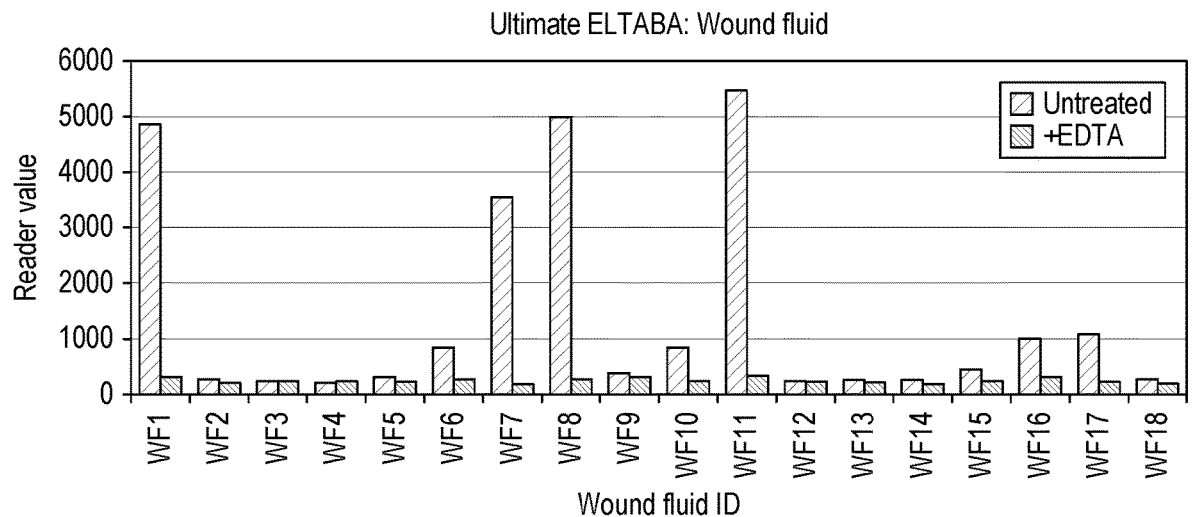
FIG. 10 is a graph comparing the ability of the assay to detect MMP activity in the presence or absence of EDTA. The graph shows that addition of EDTA to the wound samples inhibits the readout, confirming the presence of MMP in the samples and also confirming that the assay is specifically measuring active MMPs.

FIG. 10 shows that addition of EDTA to the wound samples inhibits the readout, confirming the presence of MMP in the samples and also confirms that the assay is specifically measuring active MMPs.

Example 5

Comparison of Sensitivity of the Invention to a Commercial MMP-9 Activity Assay Kit The commercial kit is designed for specifically detecting MMP-9 in biologic samples such as culture medium, serum, plasma, synovial fluid, and tissue homogenate. A monoclonal anti-human MMP is used to pull down both pro and active forms of MMP from the mixture first, and then the activity of MMP9 is quantified using fluorescence resonance energy transfer (FRET) peptide. An MMP-9 standard AMPA activated in-house was run on both the kit and a lateral flow format of the invention at a range of 250 ng/ml-4 ng/ml. For the commercial assay the MMP-9 was diluted in an MMP buffer supplied in the kit and a Tris buffer saline 1% Tween20 for lateral flow devices.

The lateral flow kit and test strip synthesis were performed as for Example 1.

Buffer standards were produced containing different concentrations of active MMP-9 (Alere San Diego) ranging from 250 ng/ml down to 4 ng/ml in a Tris buffer saline 1%

Tween (Aq. Solution of 50 mM Tris, 150 mM sodium chloride, 20 mM sodium azide, 1% vol/vol Tween 20, at pH 8.0).

STEP 1: Each standard was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad which subsequently made contact with the conjugate pad and re-hydrated the dried CF1522 antibody attached to the gold particles. Intact indicator molecule was not recognised by the gold conjugate and migrated in an uncomplexed state towards the polystreptavidin test line where it was immobilised via the biotin attached to the indicator molecule. Any MMP-9 present in the sample cleaved the indicator molecule at the cleavage site, exposing the recognisable epitope thus allowing the gold conjugate to form a complex with the cleaved stub.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually and with a Forsite Lateral flow device reader. A semi-quantitative scoring system with a scale of 0-10, in which 1 was the lowest detectable colour intensity and 10 was the highest observed colour intensity was used for the visual readings.

Figure 11A:
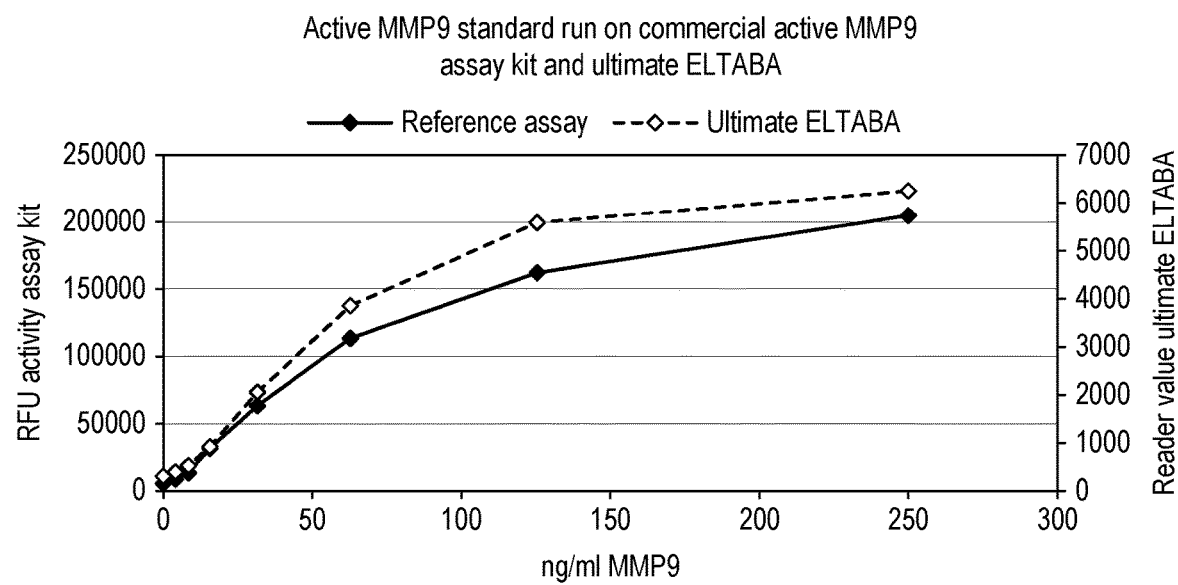
Figure 11B:
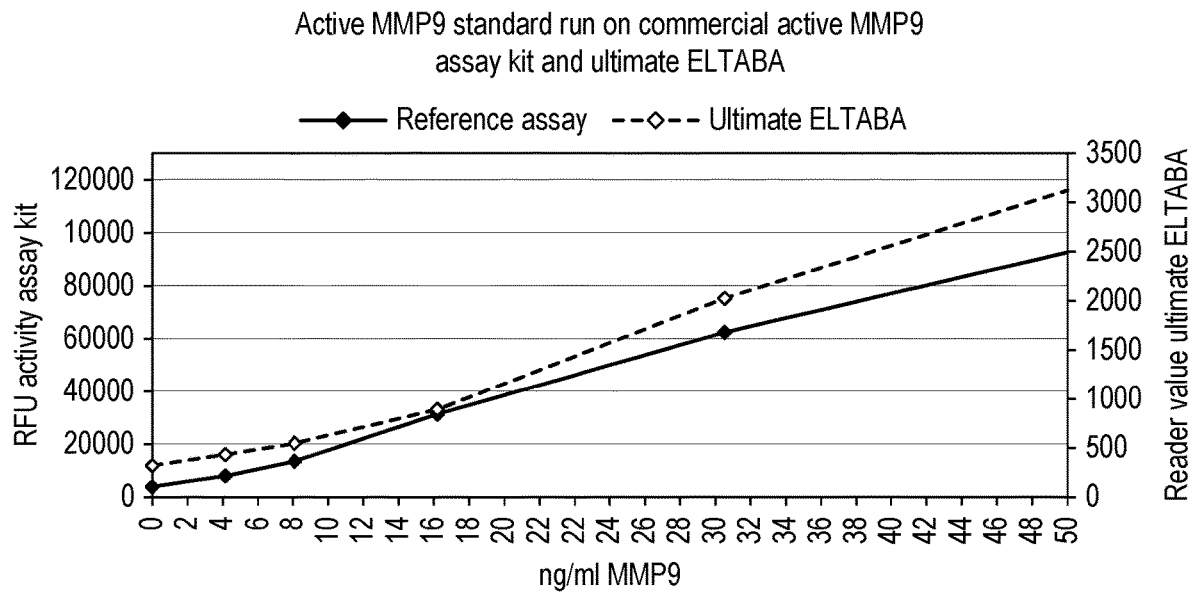
FIG. 11B is an expanded view at MMP-9 concentrations between 0 and 50 ng/ml. Both figures demonstrate that the method of the invention produced a steeper curve. According to both assays, colour development as shown by the absorbance values was seen at 4 ng/ml MMP9, the lowest standard tested.

FIG. 11 (FIGS. 11A and 11B) is a graph comparing the ability of a commercially available active MMP-9 assay kit and the assay of the invention to detect MMP9. FIG. 11A shows reader values across the entire concentration range of MMP-9, whereas FIG. 11B is an expanded view at MMP-9 concentrations between 0 and 50 ng/ml. Both figures demonstrate that the assay of the invention produced a steeper curve. According to both assays, colour development as shown by the absorbance values was seen at 4 ng/ml MMP9, the lowest standard tested.

Numerical read-outs for each assay are shown in the table below:

| ng/ml MMP9 | Reference assay | Ultimate ELTABA |
|---|---|---|
| 250 | 204466.5 | 6225 |
| 125 | 162622 | 5581 |
| 62.5 | 112706.5 | 3826 |
| 31.25 | 62301.5 | 2029 |
| 15.625 | 31295 | 882 |
| 7.8125 | 13140.5 | 524 |
| 3.90625 | 7601 | 413 |
| 0 | 3818.5 | 312 |

Example 6

Testing of Substrate in Both ELISA and LF Format

ELISA Format
1) A device for sample collection (e.g. for urine)
2) A 96 well plate coated with polystreptavidin
3) A tube, in which the sample collection device may be placed, together with the indicating molecule.
4) An indicator molecule containing the cleavable sequence, in this example, (GPQGIFGQ) which carries a terminal biotin group connected via a polyethylene glycol spacer/linker which allows it to form a complex with the capture line, polystreptavidin.
5) A sheep antibody CF1522 conjugated to alkaline phosphatase (AP)
6) An Alkaline phosphatase substrate p-nitrophenylphosphate (pNPP) that enables the development of a soluble yellow reaction product that may be read at 405 nm.

Samples were collected from healthy volunteers (9) and from patients suffering from a respiratory disease. Samples were donated from nine patients with Cystic Fibrosis (CF) and seven patients with Chronic Obstructive Pulmonary Disease (COPD) and stored at −80° C. until used.

STEP 1: Each sample was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of sample was added to the streptavidin plate (Nunc, 442404) and incubated for a further 1 hr at ambient where the biotin labelled indicator molecule becomes immobilized by the streptavidin bound to the plate.

STEP 3: The plate was washed 3 times with 100 µl in a wash buffer, Tris buffer saline 0.1% Tween (Aq. Solution of 50 mM Tris, 150 mM sodium chloride, 20 mM sodium azide, 0.1% vol/vol Tween 20, at pH 8.0).

STEP 4: CF1522-AP (Mologic) was diluted 1/500 in 1% BSA in PBST and incubated on the plate for 1 hr at ambient. The antibody will form a complex with the cleaved stubs exposed by any MMP present in the sample and in the absence of the cleaved stub there will be no binding of the antibody.

STEP 5: The plate was washed 3 times with 100 µl in a wash buffer, Tris buffer saline 0.1% Tween (Aq. Solution of 50 mM Tris, 150 mM sodium chloride, 20 mM sodium azide, 0.1% vol/vol Tween 20, at pH 8.0).

STEP 6: The plate was incubated with pNPP substrate and then read at 405 nm after 30 minute incubation at 37° C. An MMP9 standard curve is represented in FIG. 14b used as a reference. The colour of the wells indicate different levels of protease in the test sample represented by the OD 405 nm in FIG. 14b, Lateral Flow Format The kit and test strip synthesis were performed as for Example 1.

Buffer standards were produced containing different concentrations of active MMP-9 (Alere San Diego) ranging from 50 ng/ml down to 0.39 ng/ml and 62.5 ng/ml down to 0.97 ng/ml for the ELISA and lateral flow device respectively.

STEP 1: Each sample was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad which subsequently made contact with the conjugate pad and re-hydrated the dried CF1522 antibody attached to the gold particles. Intact indicator molecule was not recognised by the gold conjugate and migrated in an uncomplexed state towards the polystreptavidin test line where it was immobilised via the biotin attached to the indicator molecule. Any MMP-9 present in the sample cleaved the indicator molecule at the cleavage site, exposing the recognisable epitope thus allowing the gold conjugate to form a complex with the cleaved stub.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually and with an NES Lateral flow device reader.

Figure 12:
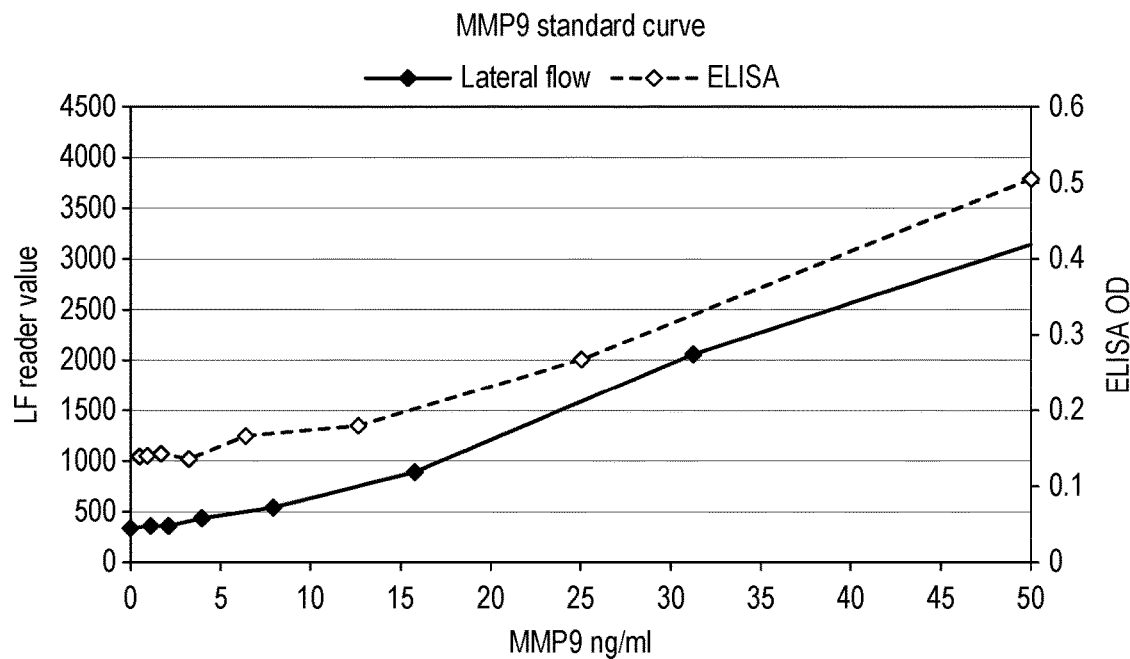
FIG. 12 shows MMP9 standard curves using ELISA and lateral flow embodiments of the invention.

The results of an MMP9 standard curve can be seen in FIG. 12. FIG. 12 demonstrates that the two MMP9 standard curves produced by the ELISA and the Lateral Flow are similar with sensitivity down to 4 ng/ml.

The numerical read-outs from the two assays are also shown in the table below:

| ELISA standard curve | | Lateral Flow standard curve | |
|---|---|---|---|
| ng/ml MMP9 | OD405 | ng/ml MMP9 | Reader value |
| 50.00 | 0.50 | 62.50 | 3826.00 |
| 25.00 | 0.27 | 31.25 | 2029.00 |
| 12.50 | 0.18 | 15.63 | 882.00 |
| 6.25 | 0.17 | 7.81 | 524.00 |
| 3.13 | 0.13 | 3.91 | 413.00 |
| 1.56 | 0.14 | 1.95 | 343.00 |
| 0.78 | 0.14 | 0.98 | 338.00 |
| 0.39 | 0.14 | 0.00 | 312.00 |

Example 7

Synthesis of an Example Indicator Molecule

Figure 16:
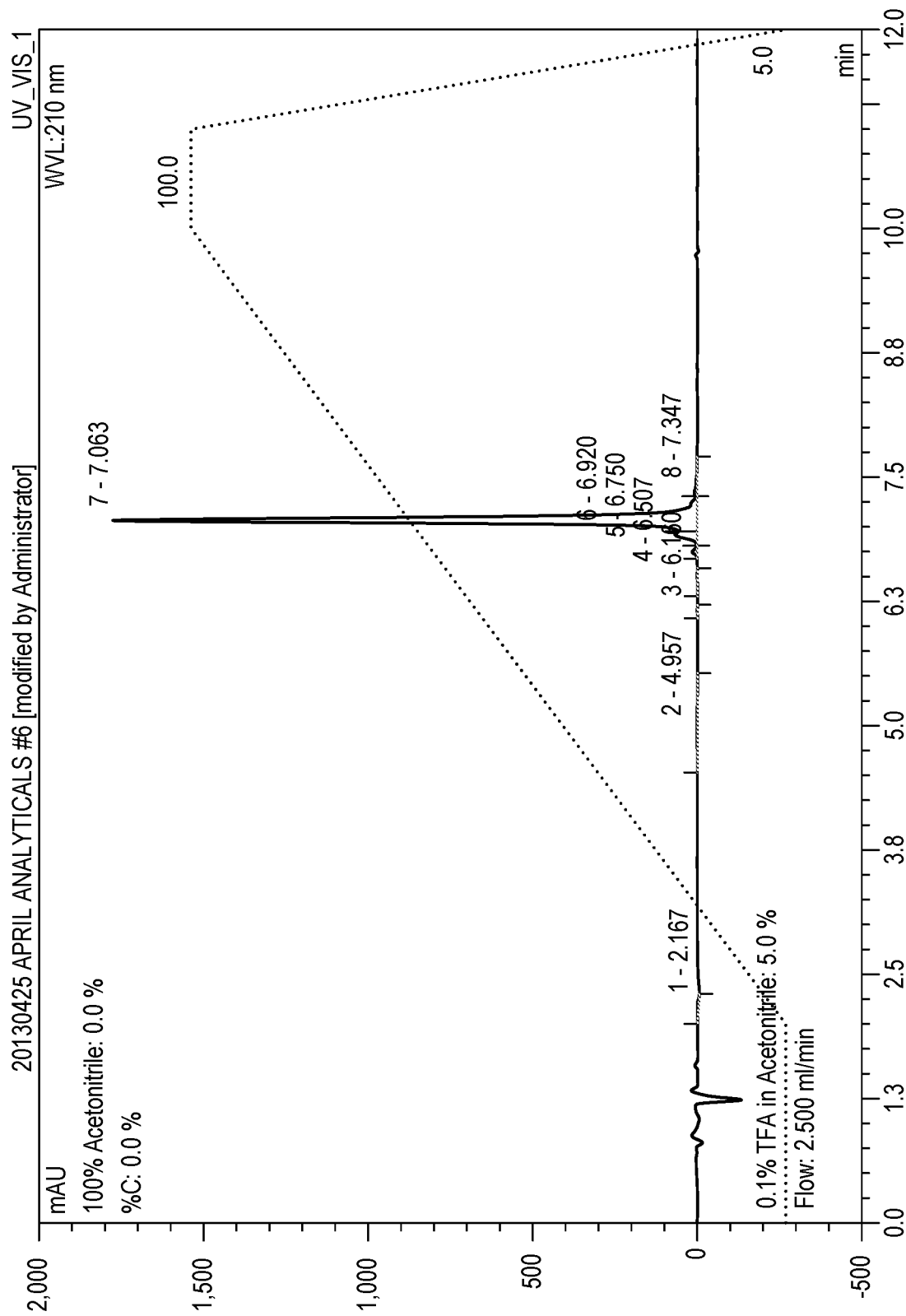
FIG. 16 shows analytical HPLC of the MOL386 peptide.
Figure 17:
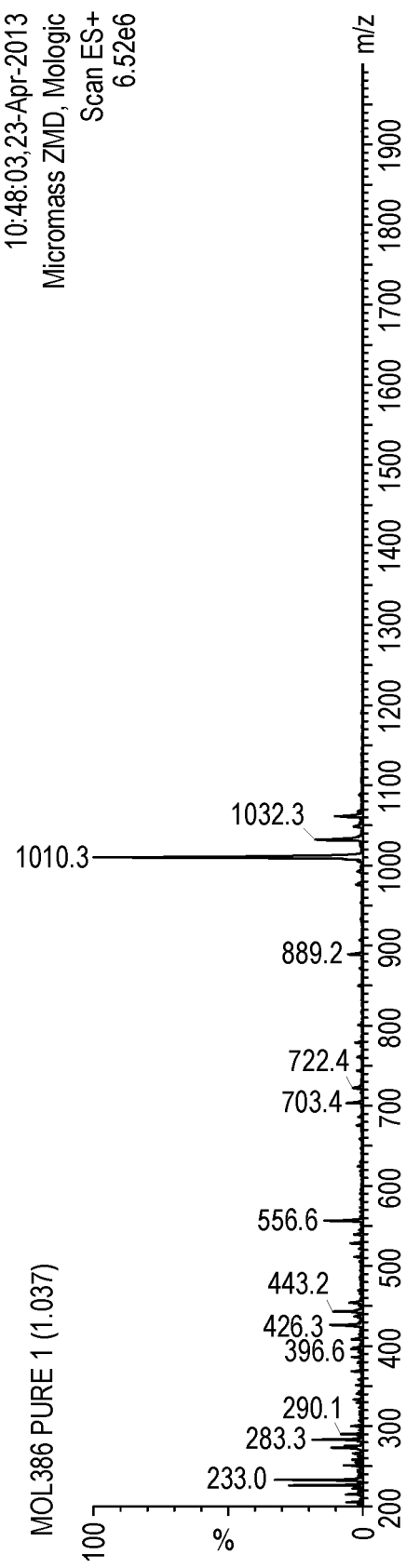
FIG. 17 is a mass spectrum of the MOL386 peptide.
Figure 18:
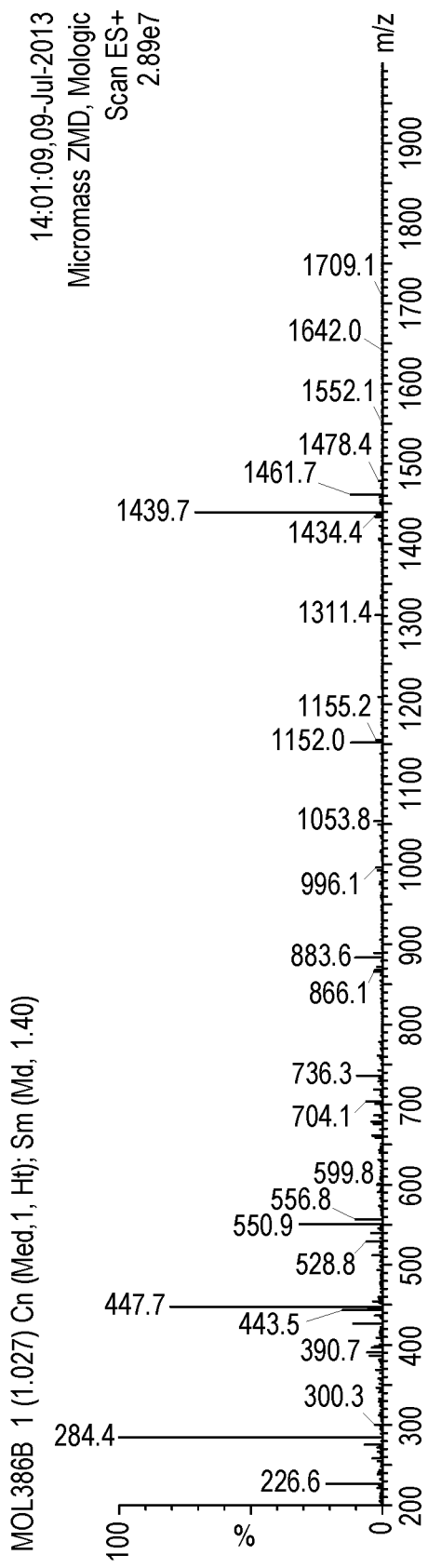
FIG. 18 is a mass spectrum of the MOL386 peptide modified with PEG-biotin.

A peptide termed MOL386 (amino acid sequence: CGPQGIFGQC) was synthesised on solid phase using Fmoc-chemistry. Briefly, synthesis was performed on a microwave assisted automated synthesiser (CEM Liberty). Coupling steps were carried out on PEG-polystyrene resin preloaded with Fmoc-Cys(Trt) in DMF solvent with a fivefold excess of amino acid building block, HBTU activator and a tenfold excess of DIPEA base. Deprotection steps were carried out in 5% Piperazine/DMF. Completed peptide resin was dried and then cleaved using 95% TFA, 2.5% TIPS and 2.5% water for 2 hours. TFA liquors were dried in vacuo and precipitated in ether to afford colourless peptide solid. Recovered peptide was freeze dried from 50% acetonitrile and purified by HPLC (FIG. 16) using a C18 reverse phase column and a gradient of 5% acetonitrile/water (0.1% TFA) to 100% acetonitrile (0.1% TFA). Isolated fractions were combined and freeze dried and analysed by electrospray mass spectrometry (FIG. 17) to identify target peptide (expected $MH_+$ 1010.17, measured 1010.3). The biotinylated form (CGPQGIFGQC-PEG-biotin) was synthesised from preloaded Biotin-PEG-NovaTag Resin (Merck) (expected $MH_+$ 1438.76, measured 1439.7, FIG. 18). The biotin provides a capture site for immobilization of the indicator molecule.

Attachment of the Scaffold Molecule (Synthesis of Cyclised Peptide)

Figure 19:
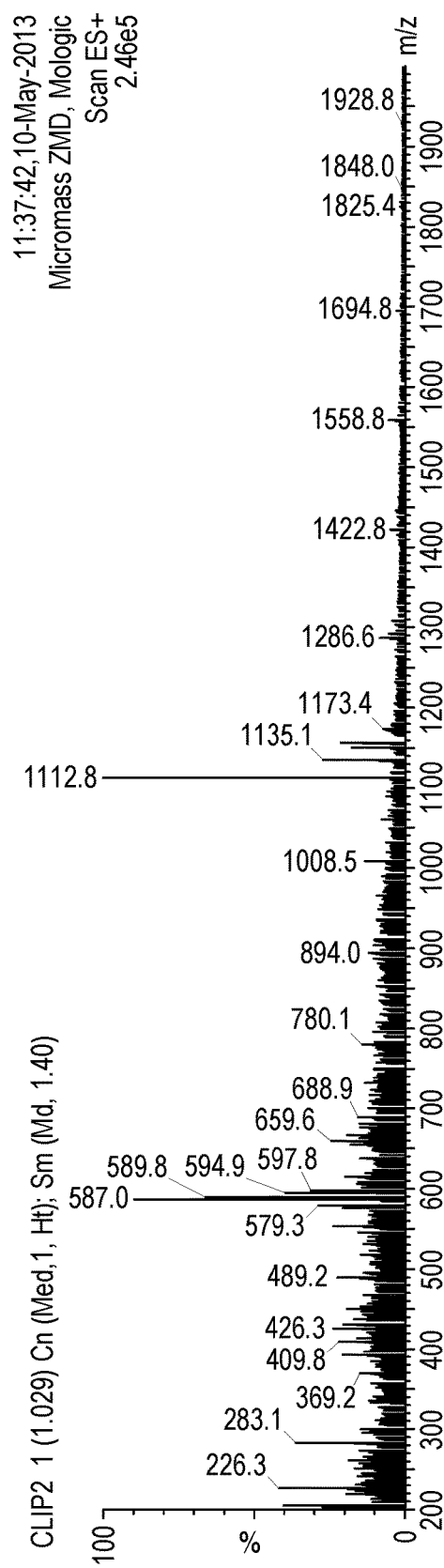
FIG. 19 is a mass spectrum analysis of the cyclised MOL386 peptide.
Figure 20:
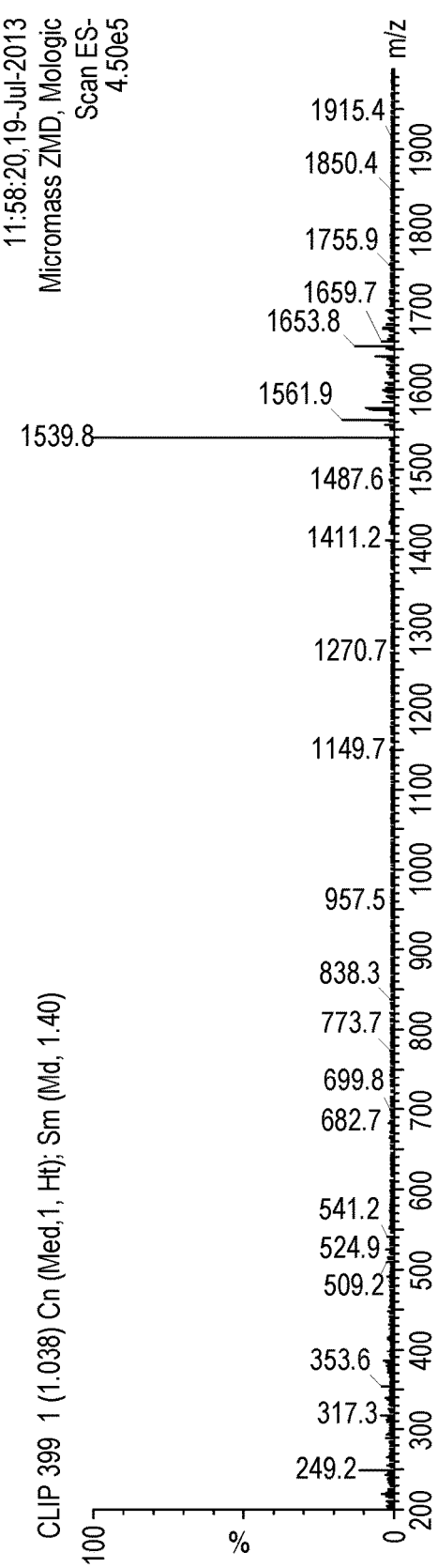
FIG. 20 is a mass spectrum analysis of the cyclised MOL386 peptide modified with PEG-biotin.

Peptide (1 mg) was dissolved in PBS 250 ul along with 1 mg of 1,3-dibromomethylbenzene and agitated gently overnight. The reaction was then diluted with 1 ml of water and injected directly on to HPLC for purification using a C18 reverse phase column and a gradient of 5% acetonitrile/water (0.1% TFA) to 100% acetonitrile (0.1% TFA). Product peak was isolated and freeze dried to afford a colourless solid (expected $MH_+$ 1112.30, measured 1112.8, FIG. 19). The same procedure was used for the biotinylated peptide (expected $MH_+$ 1540.89, measured 1539.8, FIG. 20).

Example 8

Test Format Generation

Antibodies were generated to recognise a cleaved peptide sequence. In this example (GPQGIFGQ), a target for MMP digestion, is used in an immunoassay to measure the enzyme activity in a clinical sample. The antibodies were raised to peptide KLH conjugates using methods known to those skilled in the art. Sheep antibodies CF1522 and CF1523 were generated to recognise cleaved stub 'IFGQ' whereas sheep antibodies CF1524 and CF1525 were generated to recognise cleaved stub 'GPQG'. The antibodies were affinity purified using the specific peptides they were raised against and then analysed by ELISA to determine the most appropriate assay format to give the best sensitivity.

Peptides containing the cleavable sequence (GPQGIFGQ) were synthesised with a biotin or Pegylated biotin attached to either the C-terminus (MOL038 and PCL008-A2 respectively) or the N-terminus (MOL310 and MOL378 respectively).

| Peptide | Sequence |
|---|---|
| MOL038 | Biotin-GPQGIFGQESIRLPGCPRGVNPVVS |
| PCL008-A2 | Biotin-PEG-Asp-AEEAc-AEEAc-GPQGIFGQESIRLPGCPRGVNPVVS |
| MOL310 | SIRLPGCPRGVNPVVSGPQGIFGQ-Biotin |
| MOL378 | SIRLPGCPRGVNPVVSGPQGIFGQ-AEEAc-AEEAc-PEG-Asp Biotin |

The peptide can be anchored to either streptavidin capture via the biotin or to sheep antibody CF1060 capture via the ALP sequence. The proposed formats shown schematically in FIG. 1 were evaluated.

ELISA Format
1) A device for sample collection (e.g. for urine)
2) A 96 well plate coated with polystreptavidin (Nunc, 442404) or CF1060 overnight at ambient (Nunc, Maxisorb)
3) A tube, in which the sample collection device may be placed, together with the indicating molecule.
4) An indicator molecule containing the cleavable sequence, in this example, (GPQGIFGQ) which carries a terminal biotin group which may be connected via a polyethylene glycol spacer/linker on the N or the C-terminus.
5) Sheep antibodies CF1522, CF1523, CF1524 and CF1525 conjugated to alkaline phosphatase (AP)
6) An Alkaline phosphatase substrate p-nitrophenylphosphate (pNPP) that enables the development of a soluble yellow reaction product that may be read at 405 nm.

Active MMP9 (Alere San Diego) was diluted to 2, 0.25, 0.062, 0.0156 and 0.039 μg/ml in MMP buffer (Aq. Solution of 50 mM Tris, 100 mM sodium chloride, 10 mM Calcium Chloride, 50 μM 20 mM zinc chloride, 0.025% Brij 35, 0.05% sodium azide at pH 8.0)

STEP 1: Each MMP9 standard was placed in a collection device with a defined amount of each peptide (20 ng/test). The collection device was rotated vigorously in order for the sample to mix sufficiently with the substrate solution. This reaction mixture was incubated at ambient temperature for a defined period of time (e.g. 30 minutes).

STEP 2: At the end of the incubation period, a defined volume of sample was added to the streptavidin plate and CF1060 sensitised plate and incubated for a further 1 hr at ambient where the peptides becomes immobilized by the streptavidin or CF1060 bound to the plate.

STEP 3: The plate was washed 3 times with 100 µl in a wash buffer, Tris buffer saline 0.1% Tween (Aq. Solution of 50 mM Tris, 150 mM sodium chloride, 20 mM sodium azide, 0.1% vol/vol Tween 20, at pH 8.0).

STEP 4: sheep antibodies conjugated to Alkaline Phosphatase (Mologic) were diluted 1/500 in 1% BSA in PBST and incubated on the plate for 1 hr at ambient. The antibody will form a complex with the cleaved stubs exposed by any MMP9 present in the sample, in the absence of the cleaved stub there will be no binding of the antibody.

STEP 5: The plate was washed 3 times with 100 µl in a wash buffer, Tris buffer saline 0.1% Tween (Aq. Solution of 50 mM Tris, 150 mM sodium chloride, 20 mM sodium azide, 0.1% vol/vol Tween 20, at pH 8.0).

STEP 6: The plate was incubated with pNPP substrate and then read at 405 nm after 30 minute incubation at 37° C. MMP9 standard curves are represented in FIG. 21 for all combinations. A difference in colour of the wells indicates different levels of protease in the test sample represented by the OD 405 nm.

Figure 22:
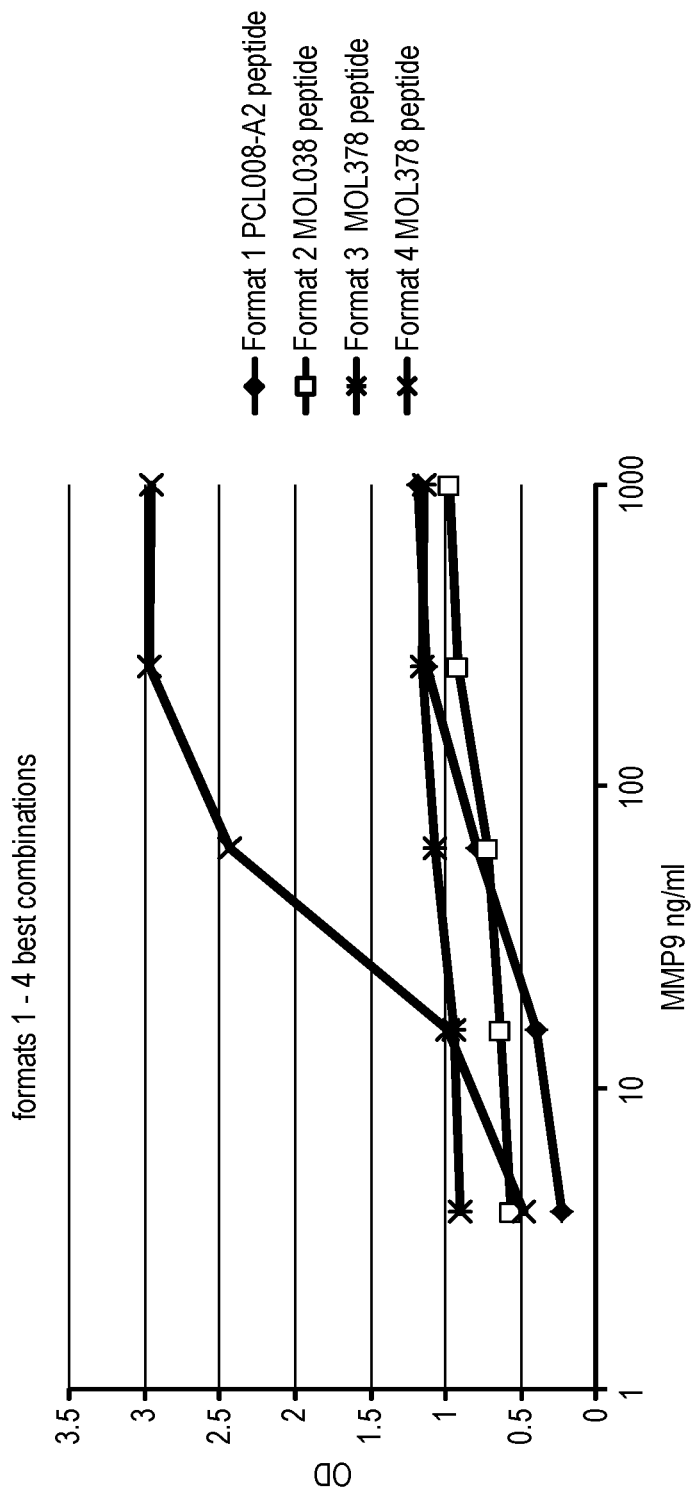
FIG. 22 presents the performance of the best combinations derived from the results shown in FIG. 21.

FIG. 21 shows the results of testing each format. With a streptavidin capture line, the selected peptide is MOL378 with sheep antibody CF1522 and PCL008-A2 with sheep antibody CF1525 as predicted. Both peptides contained a PEG-Asp-AEEAc-AEEAc required to reduce any steric hindrance. With a CF1060 capture line, the selected peptide is MOL038 or PCL008-A2 with sheep antibody CF1522 and MOL378 with sheep antibody CF1525 as predicted. The performance of the best combinations is shown in FIG. 22. Here, format 4 using sheep antibody CF1522 with peptide MOL378 shows the most promise.

Example 9

Synthesis of a Human Neutrophil Elastase Sensitive Indicator Molecule

Figure 28:
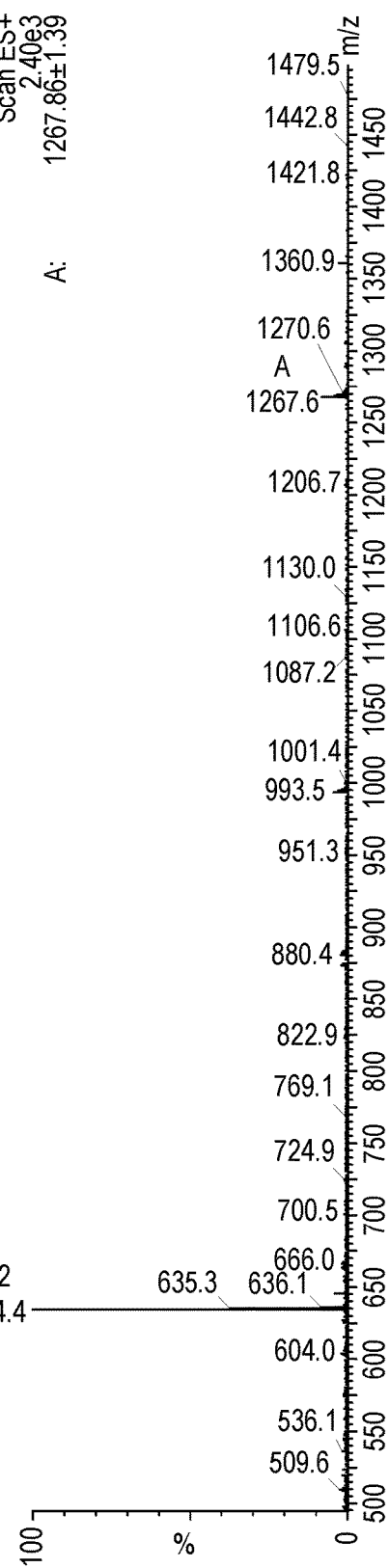
FIG. 28 shows mass spectrometric characterisation of the MOL488 peptide.

A peptide termed MOL 488 (amino acid sequence YCQE-SIRLPGC—SEQ ID NO: 4) was synthesised on solid phase using Fmoc-chemistry. Briefly, synthesis was performed on a microwave assisted automated synthesiser (CEM Liberty). Coupling steps were carried out on PEG polystyrene resin with a fivefold excess of amino acid building block, DIC and Oxyma. Deprotection steps were carried out in 20% Piperidine/DMF. Completed peptide resin was dried and then cleaved using 95% TFA, 2.5% TIPS and 2.5% water for 2 hours. TFA liquors were dried in vacuo and precipitated in ether to afford colourless peptide solid. Recovered peptide was freeze dried from 50% acetonitrile and purified by HPLC using a C18 reverse phase column and a gradient of 5% acetonitrile/water (0.1% TFA) to 100% acetonitrile (0.1% TFA). Isolated fractions were combined and freeze dried and analysed by electrospray mass spectrometry (expected $MH_+$ 1268.5, measured 1267.86±1.39)—see FIG. 28 Attachment of the Scaffold Molecule (Synthesis of Cyclised Peptide)

Figure 29:
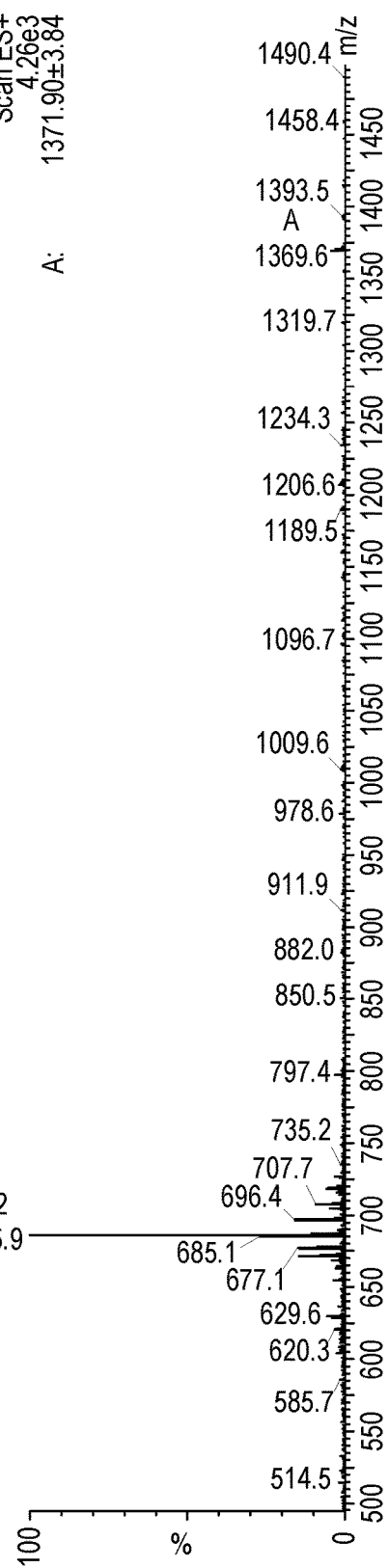
FIG. 29 shows mass spectrometric characterisation of the MOL488 peptide following attachment to the scaffold molecule (derived from 1,3-dibromomethylbenzene).

Peptide (1 mg) was dissolved in PBS 250 ul along with 1 mg of 1,3-dibromomethylbenzene and agitated gently overnight. The reaction was then diluted with 1 ml of water and injected directly on to HPLC for purification using a C18 reverse phase column and a gradient of 5% acetonitrile/water (0.1% TFA) to 100% acetonitrile (0.1% TFA). Product peak was isolated and freeze dried to afford a colourless solid (expected $MH_+$ 1370.6, measured 1371.9±3.8); see FIG. 29.

Preparative Enzymatic Cleavage of Cyclised MOL488

Figure 30:
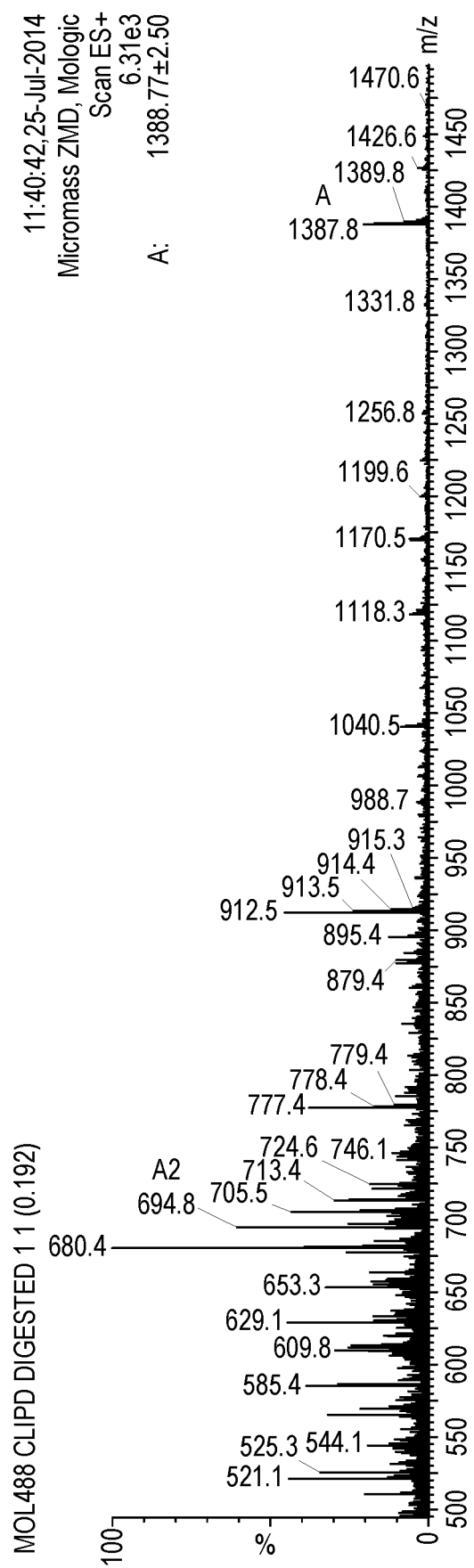
FIG. 30 shows mass spectrometric characterisation of the cyclised MOL488 peptide (i.e. attached to the scaffold) following cleavage using HNE.

Cyclised Peptide (1 mg) was dissolved in Cleavage Buffer (100 nm Tris pH 8.0. 0.05% Brij) at a final concentration of 5 mg/ml. Enzyme Human Neutrophil elastase (Leeblo Solutions inc.) was added to a final concentration of U/ml. To follow reaction progress timed aliquots were quenched in 5 volumes of starting buffer (5% acetonitrile, 0.1% TFA) and checked on HPLC. A new product peak evolved over time and after approximately three hours the reaction was stopped and the product fraction purified by HPLC (expected $MH_+$ 1388.6, measured 1388.8±2.5)—see FIG. 30.

The same procedure was also followed in respect of a similar substrate but in this case lacking the tyrosine residue (SEQ ID NO: 3).

Figure 24A:
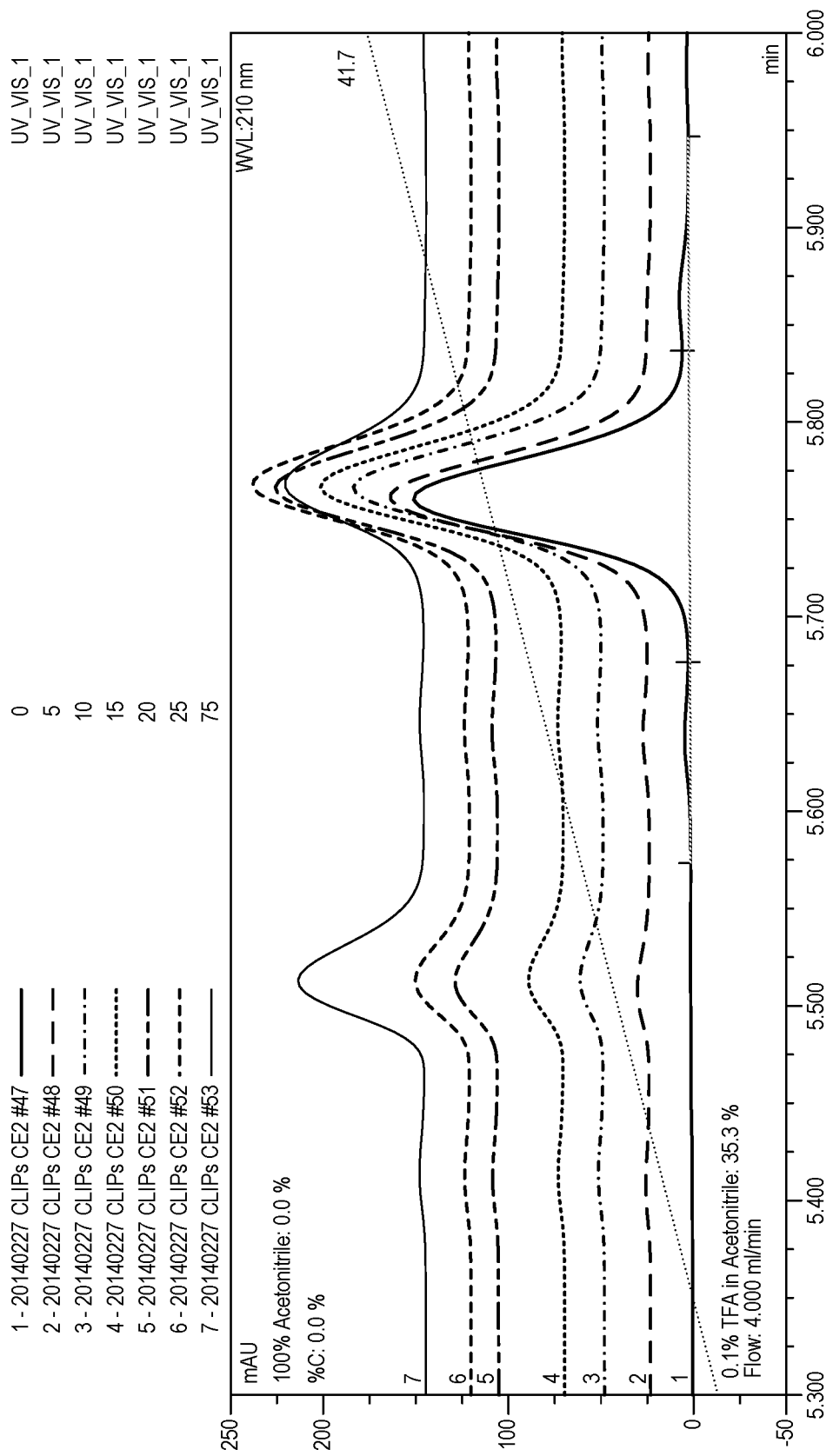
FIG. 24A presents the raw plot data.
Figure 24B:
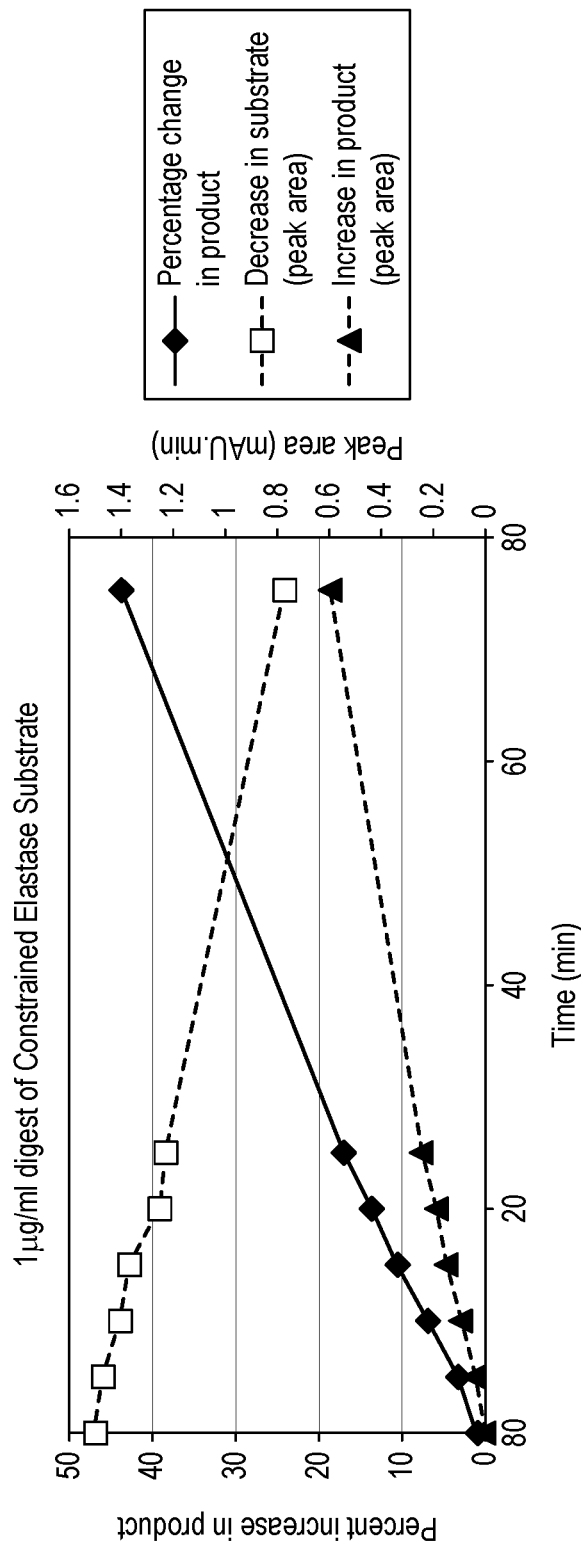
FIG. 24B presents a time course showing the relative increase in product and decrease in substrate over time.

HPLC results are summarised in FIG. 24. It can be seen from FIG. 24A that a single cleavage product results from HNE activity on the peptide. FIG. 24B presents a time course showing the relative increase in product and decrease in substrate over time.

Figure 25A:
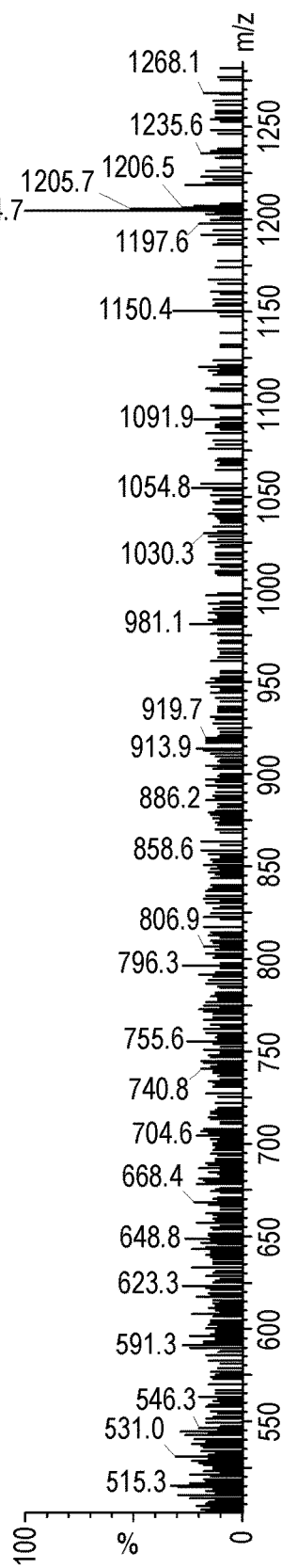
FIG. 25A is the substrate plot and FIG. 25B is the hydrolysed product.
Figure 25B:
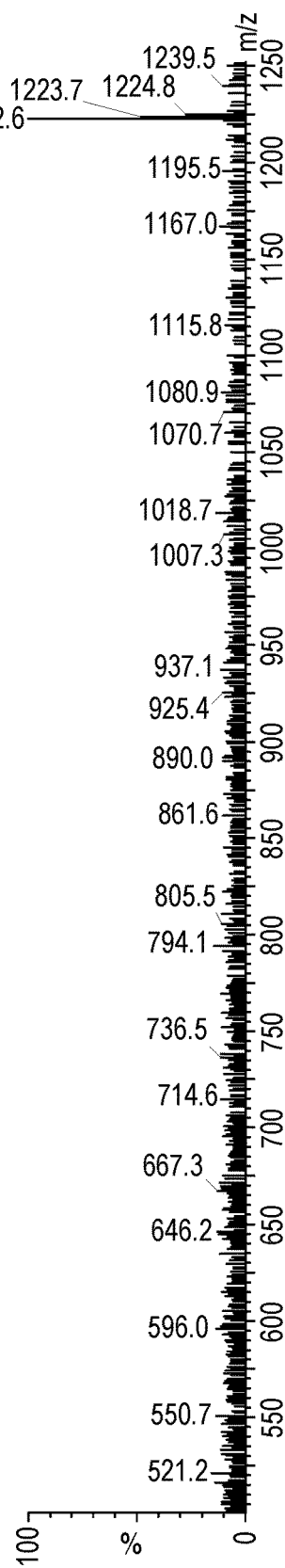

FIG. 25 presents mass spectrometric data confirming that the substrate is cleaved at a single site and that the substrate otherwise remains intact. FIG. 25A is the substrate plot and FIG. 25B is the hydrolysed product.

Example 10

Conjugation Methods

Figure 26:
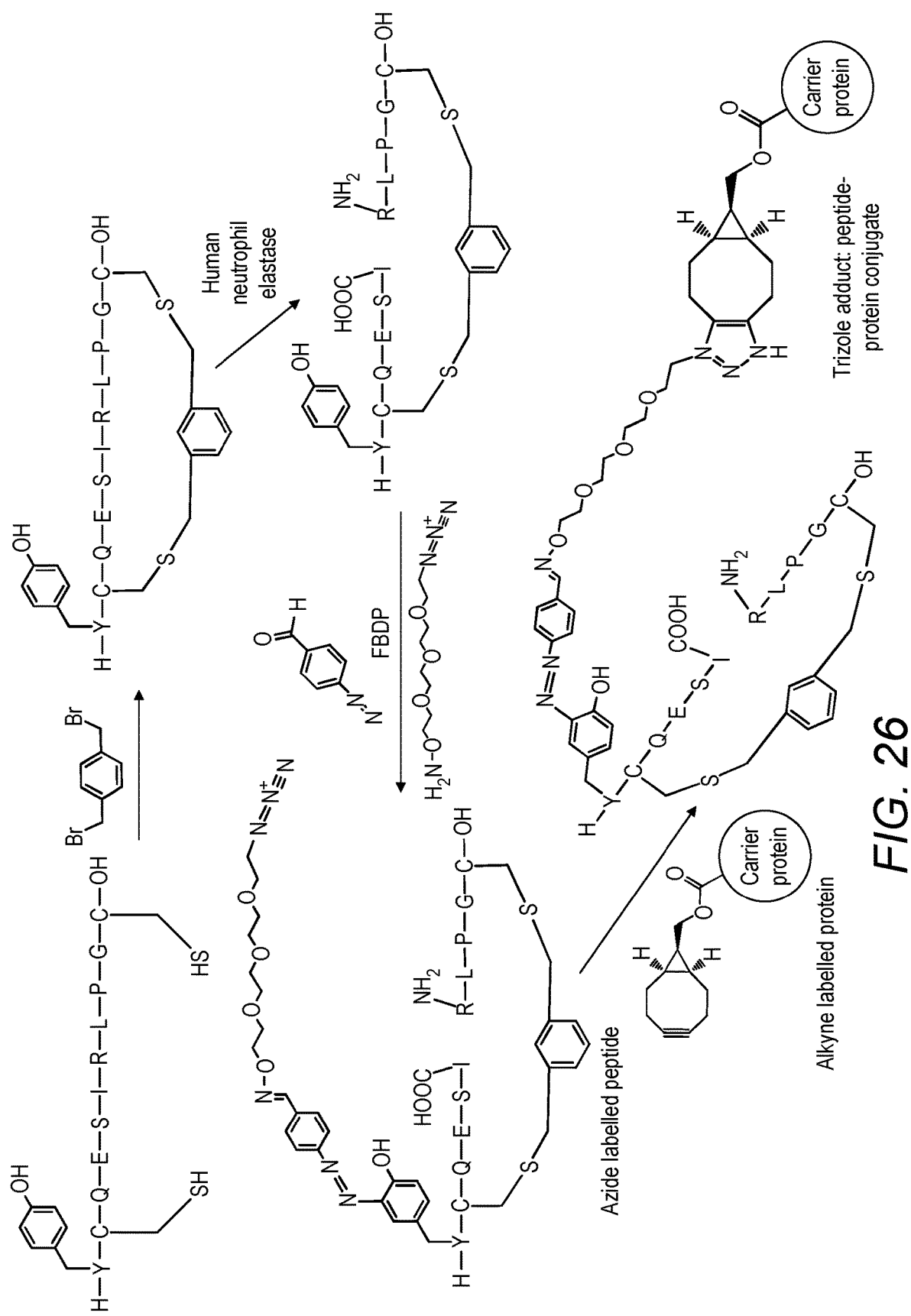
FIG. 26 presents one route for generating an immunogen to raise antibodies specific for the cleaved form of the indicator molecule shown in FIG. 23.
Figure 27:
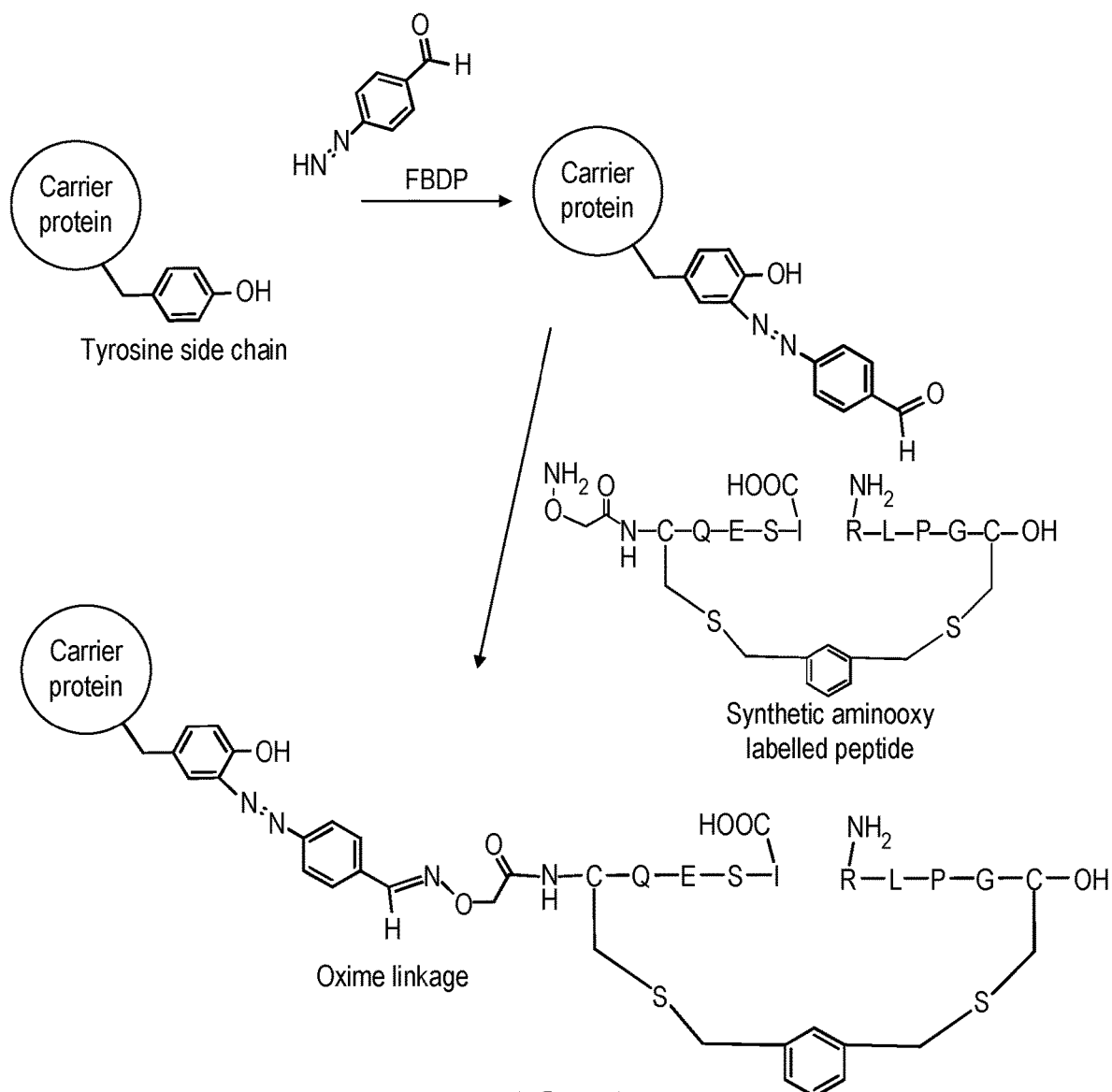
FIG. 27 presents an alternative route for generating an immunogen to raise antibodies specific for the cleaved form of the indicator molecule shown in FIG. 23.

To conjugate the protease-digested peptide product to a carrier protein to immunise and develop antibodies, a chemistry orthogonal to the Clip thiol alkylation route needs to be applied. A combination of three different chemistries (diazo, oxime and triazole) are considered in this instance to achieve conjugation. In the first option (FIG. 26) the peptide can be synthesised with a pendant tyrosine residue. The heterobifunctional reagent FBDP (Sigma) is used to conjugate an aminooxy linker (Berry Associates) on to the phenol group of the tyrosine creating a pendant azide tail. This in turn can be conjugated to a carrier protein labelled with an alkyne reagent. Alternatively, the peptide can be synthesised with an aminooxy terminus (FIG. 27) and this can then be crosslinked directly to tyrosine residues on the carrier protein using the FBDP reagent.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all aspects and embodiments of the invention described herein are considered to be broadly applicable and combinable with any and all other consistent embodiments, including those taken from other aspects of the invention (including in isolation) as appropriate. Various publications are cited herein, the disclosures of which are incorporated by reference in their entireties.

The invention claimed is:

1. An enzyme detection kit for detecting the presence of cleavage activity of an enzyme, the kit comprising:
   (i) an intact indicator molecule, the intact indicator molecule comprising
      (a) a cleavage region comprising at least one cleavage site that is specific for the enzyme, the cleavage region defining an end of a detectable fragment or cleavage part of the indicator molecule when the intact indicator molecule is cleaved at the cleavage site, the detectable fragment or cleavage part of the indicator molecule comprising a binding site, wherein the binding site of the detectable fragment or cleavage part of the indicator molecule is a conformational epitope that is not formed in the intact indicator molecule; and
      (b) a capture site which is present in the intact indicator molecule and is present in the detectable fragment or cleavage part of the indicator molecule;
   (ii) capture molecules which are (a) capable of binding to the capture site of the intact indicator molecule and (b) capable of binding to the capture site of the detectable fragment or cleavage part of the indicator molecule;
   (iii) a solid support to which the capture molecules are attachable or attached to form a capture zone; and
   (iv) binding molecules which are (a) capable of binding to the binding site of the detectable fragment or cleavage part of the indicator molecule and (b) incapable of binding to the intact indicator molecule.

* * * * *